United States Patent
Mujica-Fernaud et al.

(10) Patent No.: US 10,032,992 B2
(45) Date of Patent: Jul. 24, 2018

(54) COMPOUNDS FOR ORGANIC ELECTROLUMINESCENT DEVICES

(71) Applicant: Merck Patent GmbH, Darmstadt (DE)

(72) Inventors: Teresa Mujica-Fernaud, Darmstadt (DE); Amir Hossain Parham, Frankfurt am Main (DE); Philipp Stoessel, Frankfurt am Main (DE); Christof Pflumm, Darmstadt (DE); Arne Buesing, Frankfurt am Main (DE); Thomas Eberle, Landau (DE)

(73) Assignee: Merck Patent GmbH, Darmstadt (DE)

( * ) Notice: Subject to any disclaimer, the term of this patent is extended or adjusted under 35 U.S.C. 154(b) by 988 days.

(21) Appl. No.: 14/366,513

(22) PCT Filed: Nov. 26, 2012

(86) PCT No.: PCT/EP2012/004879
§ 371 (c)(1),
(2) Date: Jun. 18, 2014

(87) PCT Pub. No.: WO2013/091762
PCT Pub. Date: Jun. 27, 2013

(65) Prior Publication Data
US 2014/0361224 A1  Dec. 11, 2014

(30) Foreign Application Priority Data
Dec. 22, 2011 (EP) .................................. 11010103

(51) Int. Cl.
*C07D 239/26* (2006.01)
*C07F 5/02* (2006.01)
*H01L 51/00* (2006.01)
*H01L 51/50* (2006.01)

(52) U.S. Cl.
CPC ........ *H01L 51/0071* (2013.01); *C07D 239/26* (2013.01); *C07F 5/02* (2013.01); *C07F 5/027* (2013.01); *H01L 51/008* (2013.01); *H01L 51/0067* (2013.01); *H01L 51/0059* (2013.01); *H01L 51/0085* (2013.01); *H01L 51/5016* (2013.01); *H01L 2251/5384* (2013.01); *Y02E 10/549* (2013.01)

(58) Field of Classification Search
None
See application file for complete search history.

(56) References Cited

U.S. PATENT DOCUMENTS

2012/0056169 A1    3/2012 Kaiser et al.

FOREIGN PATENT DOCUMENTS

WO    WO-2010/108579 A1    9/2010

OTHER PUBLICATIONS

Tian et al., JACS, 2012, 134, 14666-14669.*
Weber et al., "N-Aryl- and N-Thienylcarbazoles with Dimesitylboryl and 1,3,2-Benzocliazaborolyl Functions", *Eur. J. Inorg. Chem.*, pp. 3091-3101 (2011).
Weber et al., "Syntheses, Structure, Electrochemistry, and Optical Properties of 1,3-Diethyl-2,3-dihydro-1-H-1,3,2-pyrido-[4,5-b]-diazaboroles", *Z. Anorg. Allg. Chem.*, vol. 634, pp. 1729-1734 (2008).
Weber et al., "1,3,2-Diazaborolyl-functionalized thiophenes and dithiophenes: synthesis, structure, electrochemistry and luminescence", *Dalton Trans.*, pp. 3777-3784 (2006).
International Search Report for PCT/EP2012/004879 dated Jan. 30, 2013.
Weber, L., et al., "Synthetic, structural, photophysical and computational studies of π-conjugated bis- and tris-1,3,2-benzodiazaboroles and related bis(boryl) dithiophenes", Dalton Transactions, No. 8, (2009), pp. 1339-1351.
Weber, L., et al., "Synthetic, structural, Photophysical and Computational Studies on π-Conjugated 1,3,2-Benzodiazaboroles with Carbazole Building Blocks", European Journal of Inorganic Chemistry, vol. 2010, No. 34, (2010), pp. 5416-5425.

* cited by examiner

*Primary Examiner* — Alicia L Otton
(74) *Attorney, Agent, or Firm* — Drinker Biddle & Reath LLP

(57) ABSTRACT

The present invention relates to boron compounds for use in electronic devices, especially organic electroluminescent devices, and to a process for preparing these compounds and to electronic devices, especially organic electroluminescent devices, comprising these compounds.

Formel (1)

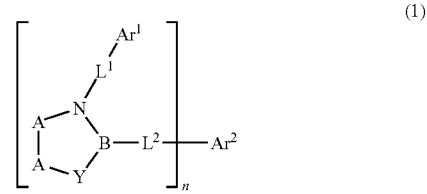

18 Claims, No Drawings

COMPOUNDS FOR ORGANIC ELECTROLUMINESCENT DEVICES

CROSS-REFERENCE TO RELATED APPLICATIONS

This application is a national stage application (under 35 U.S.C. § 371) of PCT/EP2012/004879, filed Nov. 26, 2012, which claims benefit of European Application No. 11010103.7, filed Dec. 22, 2011.

The present invention relates to materials for use in electronic devices, to a process for the preparation of these materials and to electronic devices, in particular organic electroluminescent devices, comprising these materials.

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO 98/27136. The emitting materials employed here are increasingly organometallic complexes which exhibit phosphorescence instead of fluorescence (M. A. Baldo et al., *Appl. Phys. Lett.* 1999, 75, 4-6). For quantum-mechanical reasons, an up to four-fold energy and power efficiency is possible using organometallic compounds as phosphorescence emitters. In general, however, there is still a need for improvement, in particular with respect to efficiency, operating voltage and lifetime, in the case of OLEDs, in particular also in the case of OLEDs which exhibit triplet emission. This applies, in particular, to OLEDs which emit in the relatively short-wave region, i.e. green or blue.

The properties of phosphorescent OLEDs are determined not only by the triplet emitters employed. In particular, the other materials used, such as matrix materials, hole-blocking materials, electron-transport materials, hole-transport materials and electron- or exciton-blocking materials, are also of particular importance here. Improvements in these materials can thus also result in significant improvements in the OLED properties. There is also still a need for improvement in the case of these materials for fluorescent OLEDs.

In accordance with the prior art, ketones (for example in accordance with WO 2004/093207 or WO 2010/006680), inter alia, are used as matrix materials for phosphorescent emitters. Furthermore, boronic acid derivatives (for example in accordance with WO 2006/117052) or diazaphosphole derivatives (for example in accordance with WO 2010/054730) are known as matrix materials for phosphorescent emitters.

However, there is still a need for improvement, in particular with respect to the efficiency and the lifetime of the device, in the case of use of all these matrix materials as in the case of other matrix materials.

The object of the present invention is the provision of compounds which are suitable for use in a fluorescent or phosphorescent OLED, in particular a phosphorescent OLED, for example as matrix material or as hole-transport/ electron-blocking material or exciton-blocking material or as electron-transport or hole-blocking material. In particular, it is the object of the present invention to provide matrix materials which are potentially also suitable for blue- and green-phosphorescent OLEDs.

Surprisingly, it has been found that the compounds described in greater detail below achieve this object and result in improvements in the organic electroluminescent device, in particular with respect to the lifetime, the efficiency and/or the operating voltage. This applies, in particular, in the case of use of the compounds according to the invention as matrix material. In particular, it has been found here that the compounds according to the invention give better results than the boronic acid derivatives described in WO 2006/117052. The present invention therefore relates to these compounds and to organic electroluminescent devices which comprise compounds of this type.

The present invention relates to a compound of the following formula (1),

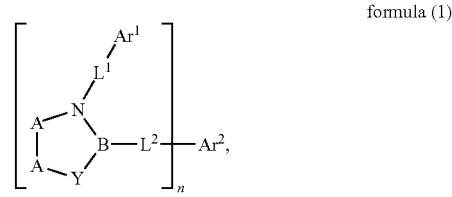

formula (1)

where the following applies to the symbols and indices used:

A-A is, identically or differently on each occurrence, a unit of the following formula (2), (3), (4), (5), (6), (7) or (8),

Formel (2)

Formel (3)

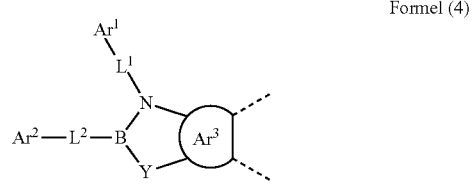

Formel (4)

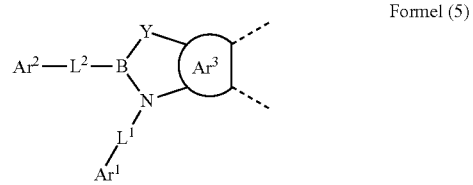

Formel (5)

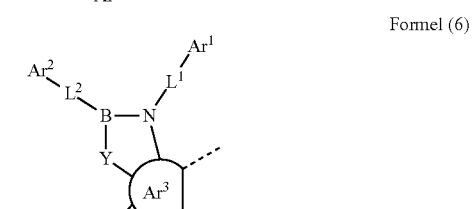

Formel (6)

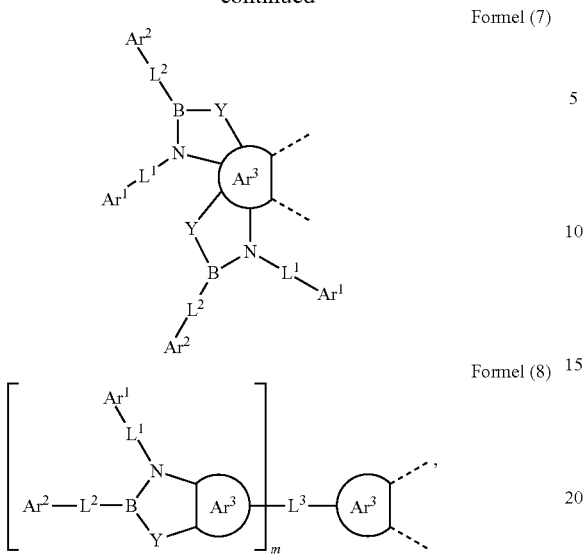

Formel (7)

Formel (8)

where the dashed bond in each case represents the link to N or Y;

Y is, identically or differently on each occurrence, N—R², O or S;

Ar¹, Ar² is on each occurrence, identically or differently, an aryl or heteroaryl group having 5 to 18 aromatic ring atoms, which may be substituted by one or more radicals R¹;

Ar³ is on each occurrence, identically or differently, an aryl or heteroaryl group having 5 to 14 aromatic ring atoms, which may be substituted by one or more radicals R¹;

L¹, L² is on each occurrence, identically or differently, a single bond or a divalent aromatic or heteroaromatic ring system having 5 to 24 aromatic ring atoms, which may be substituted by one or more radicals R¹;

L³ is a single bond or a divalent, trivalent or tetravalent group;

R¹ is selected on each occurrence, identically or differently, from the group consisting of H, D, F, Cl, Br, I, CN, NO₂, N(R³)₂, C(=O)R³, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals R³, where one or more non-adjacent CH₂ groups may be replaced by R³C=CR³, C≡C, Si(R³)₂, Ge(R³)₂, Sn(R³)₂, C=O, C=S, C=Se, C=NR³, P(=O)(R³), SO, SO₂, NR³, O, S or CONR³ and where one or more H atoms may be replaced by D, F, Cl, Br, I, CN or NO₂, an aromatic or heteroaromatic ring system having 5 to 60 aromatic ring atoms, which may in each case be substituted by one or more radicals R³, an aryloxy or heteroaryloxy group having 5 to 60 aromatic ring atoms, which may be substituted by one or more radicals R³, or a combination of these systems, where two or more adjacent substituents R¹ may optionally form a monocyclic or polycyclic, aliphatic, aromatic or heteroaromatic ring system, which may be substituted by one or more radicals R³;

R² is selected on each occurrence, identically or differently, from the group consisting of a straight-chain alkyl group having 1 to 40 C atoms or a branched or cyclic alkyl group having 3 to 40 C atoms, each of which may be substituted by one or more radicals R³, where one or more non-adjacent CH₂ groups may be replaced by R³C=CR³, C≡C or C=O and where one or more H atoms may be replaced by D, F, Cl, Br, I, CN or NO₂, an aromatic or heteroaromatic ring system having 5 to 60 aromatic ring atoms, which may in each case be substituted by one or more radicals R³, or a combination of these systems; the R¹ and R² that are adjacent to one another in the 1,2-position may optionally form a monocyclic or polycyclic, aliphatic, aromatic or heteroaromatic ring system here, which be substituted by one or more radicals R³;

R³ is selected from the group consisting of H, D, F, CN, aliphatic hydrocarbon radical having 1 to 20 C atoms, aromatic or heteroaromatic ring system having 5 to 30 aromatic ring atoms, in which one or more H atoms may be replaced by D, F, Cl, Br, I or CN, where two or more adjacent substituents R³ may form a mono- or polycyclic, aliphatic, aromatic or heteroaromatic ring system with one another;

n is 1, 2, 3, 4, 5 or 6;

m is 1 if L³ is a single bond or a divalent group, or is 2 if L³ is a trivalent group, or is 3 if L³ is a tetravalent group;

characterised in that at least one group Ar¹ is present which stands for a heteroaryl group having 5 to 18 aromatic ring atoms, which may also be substituted by one or more radicals R¹, or in that at least one group Ar² is present which stands for an electron-deficient heteroaryl group having 5 to 18 aromatic ring atoms.

An aryl group in the sense of this invention contains 6 to 60 C atoms; a heteroaryl group in the sense of this invention contains 2 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (fused) aryl or heteroaryl group, for example naphthalene, anthracene, phenanthrene, quinoline, isoquinoline, etc. Aromatic rings linked to one another by a single bond, such as, for example, biphenyl, are, by contrast, not referred to as an aryl or heteroaryl group, but instead as an aromatic ring system.

An electron-deficient heteroaryl group in the sense of the present invention is defined as a 5-membered ring heteroaryl group having at least two heteroatoms, for example imidazole, oxazole, oxadiazole, etc., or as a 6-membered ring heteroaryl group having at least one heteroatom, for example pyridine, pyrimidine, pyrazine, triazine, etc. Further 6-membered ring aryl or 6-membered ring heteroaryl groups may also be condensed onto these groups, as is the case, for example, in benzimidazole, quinoline or phenanthroline.

An aromatic ring system in the sense of this invention contains 6 to 60 C atoms in the ring system. A heteroaromatic ring system in the sense of this invention contains 2 to 60 C atoms and at least one heteroatom in the ring system, with the proviso that the sum of C atoms and heteroatoms is at least 5. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be interrupted by a non-aromatic unit (preferably less than 10% of the atoms other than H), such as, for example, an sp³-hybridised C, N or O atom. Thus, for example, systems such as fluorene, 9,9'-spirobifluorene, 9,9-diarylfluorene, triarylamine, diaryl ether, stilbene, etc., are also intended to be taken to be aromatic ring systems in the sense of this invention, as are systems in which two or more aryl groups are interrupted, for example, by a short alkyl group.

For the purposes of the present invention, an aliphatic hydrocarbon radical or an alkyl group or an alkenyl or alkynyl group, which may typically contain 1 to 40 or also 1 to 20 C atoms and in which, in addition, individual H atoms or CH$_2$ groups may be substituted by the above-mentioned groups, is preferably taken to mean the radicals methyl, ethyl, n-propyl, i-propyl, n-butyl, i-butyl, s-butyl, t-butyl, 2-methylbutyl, n-pentyl, s-pentyl, cyclo-pentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, hep-tenyl, cycloheptenyl, octenyl, cyclooctenyl, ethynyl, propynyl, butynyl, pen-tynyl, hexynyl, heptynyl or octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy or 2,2,2-trifluoroethoxy. A thioalkyl group having 1 to 40 C atoms is taken to mean, in particular, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoro-ethylthio, ethenylthio, propenylthio, butenylthio, pentenylthio, cyclo-pentenylthio, hexenylthio, cyclohexenylthio, heptenylthio, cycloheptenyl-thio, octenylthio, cyclooctenylthio, ethynylthio, propynylthio, butynylthio, pentynylthio, hexynylthio, heptynylthio or octynylthio. In general, alkyl, alkoxy or thioalkyl groups may in accordance with the present invention be straight-chain, branched or cyclic, where one or more non-adjacent CH$_2$ groups may be replaced by $R^3C=CR^3$, C≡C, Si($R^3$)$_2$, Ge($R^3$)$_2$, Sn($R^3$)$_2$, C=O, C=S, C=Se, C=NR$^3$, P(=O)(R$^3$), SO, SO$_2$, NR$^3$, O, S or CONR$^3$; furthermore, one or more H atoms may also be replaced by D, F, Cl, Br, I, CN or NO$_2$, preferably F, Cl or CN, furthermore preferably F or CN, particularly preferably CN.

An aromatic or heteroaromatic ring system having 5-60 aromatic ring atoms, which may also in each case be substituted by the above-mentioned radicals R$^3$ or a hydrocarbon radical and which may be linked via any desired positions on the aromatic or heteroaromatic group, is taken to mean, in particular, groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spiro-truxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxa-zole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothia-diazole.

If the compound of the formula (1) contains a unit of one or more of the formulae (2) or (4) to (8), Ar$^3$ preferably stands, identically or differently on each occurrence, for an aryl or heteroaryl group having 5 to 10 aromatic ring atoms, particularly preferably having 5 or 6 aromatic ring atoms. Preferred aryl and heteroaryl groups Ar$^3$ are selected, identically or differently on each occurrence, from the group consisting of benzene, pyridine, pyrimidine, pyridazine, pyrazine, furan, thiophene, pyrrole, naphthalene, phenanthrene, quinoline, isoquinoline, quinoxaline, indole, benzofuran and benzothiophene. The aryl or heteroaryl group here preferably contains no six-membered rings condensed directly onto one another. Particularly preferred aryl and heteroaryl groups Ar$^3$ are selected, identically or differently on each occurrence, from the group consisting of benzene, pyridine, pyrimidine and pyrazine, in particular benzene.

Preferred embodiments of the compounds of the above-mentioned formula (1) are the compounds of the formulae (9) to (18),

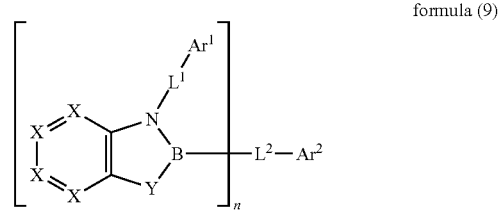

formula (9)

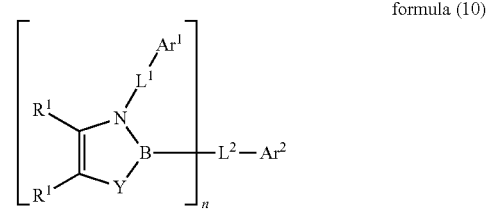

formula (10)

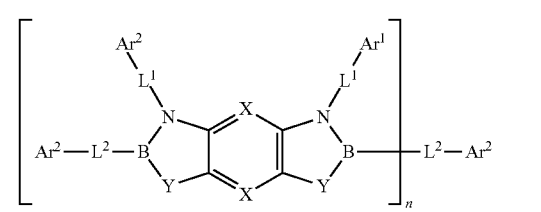

formula (11)

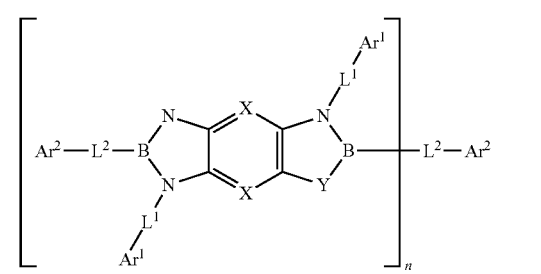

formula (12)

formula (13)
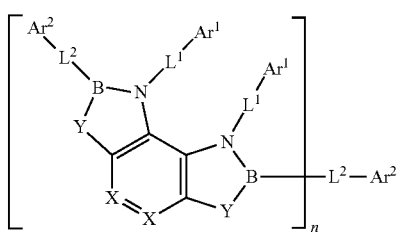

formula (14)
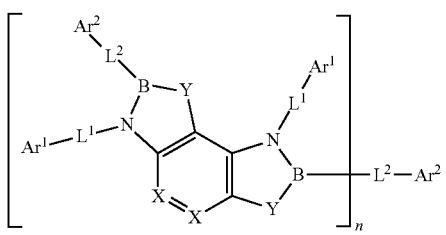

formula (15)
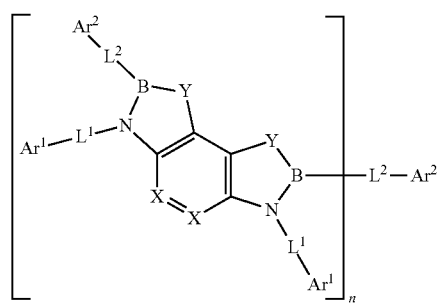

formula (16)
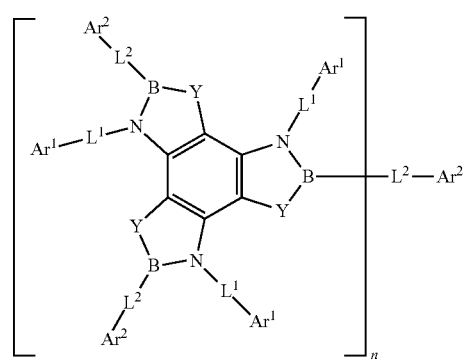

formula (17)
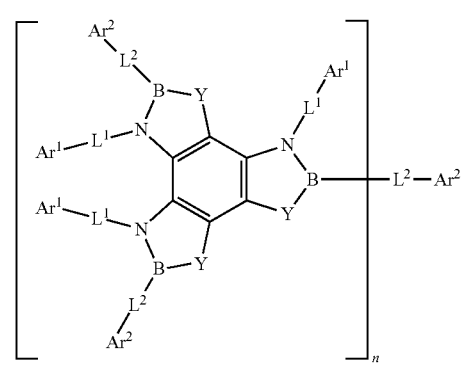

formula (18)
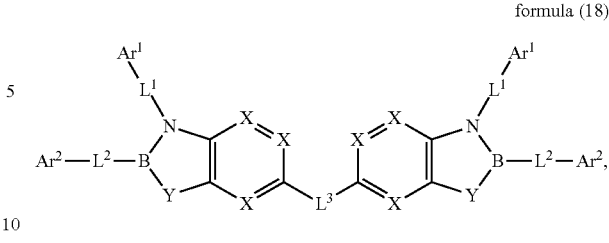

where X is on each occurrence, identically or differently, $CR^1$ or N and the other the symbols and indices used have the meanings given above.

In a preferred embodiment of the compounds of the formula (1) or formula (9) to (18), the symbol Y stands, identically or differently on each occurrence, for $N-R^2$. Correspondingly, the symbol Y in the sub-units of the formulae (4) to (8) also preferably stands, identically or differently on each occurrence, for $N-R^2$.

In a further preferred embodiment of the invention, $L^1$ or $L^2$ stands, identically or differently on each occurrence, for a single bond or a divalent arylene or heteroarylene group having 5 to 10 aromatic ring atoms, which may in each case be substituted by one or more radicals $R^1$. $L^1$ or $L^2$ particularly preferably stands, identically or differently on each occurrence, for a divalent arylene or heteroarylene group having 6 aromatic ring atoms, which may be substituted by one or more radicals $R^1$, but is preferably unsubstituted, in particular for 1,2-, 1,3- or 1,4-phenylene, pyridine, pyrimidine or triazine, very particularly preferably for phenylene or pyridine.

In a further preferred embodiment of the compounds of the formula (1) or formula (18), $L^3$ stands for a single bond, O, S, $NR^2$, an alkylene group having 1 to 10 C atoms, which may be substituted by one or more radicals $R^3$, or an aromatic or heteroaromatic ring system having 5 to 30 aromatic ring atoms, which may be substituted by one or more radicals $R^3$.

In a further preferred embodiment of the invention, a maximum of two symbols X in each ring stand for N and the other symbols X stand, identically or differently on each occurrence, for $CR^1$. Particularly preferably, a maximum of one symbol X in each ring stands for N and the other symbols X stand, identically or differently on each occurrence, for $CR^1$. Very particularly preferably, all symbols X stand, identically or differently on each occurrence, for $CR^1$.

In a further preferred embodiment of the invention, the group $Ar^1$ or $Ar^2$ stands, identically or differently on each occurrence, for an aromatic or heteroaromatic ring system having 5 to 24 aromatic ring atoms, particularly preferably having 5 to 18 aromatic ring atoms, where the aromatic or heteroaromatic ring system may in each case also be substituted by one or more radicals $R^1$. $Ar^1$ or $Ar^2$ is particularly preferably, identically or differently on each occurrence, an aryl or heteroaryl group having 5 to 13 aromatic ring atoms, which may in each case also be substituted by one or more radicals $R^1$. $Ar^1$ or $Ar^2$ here preferably contains no aryl or heteroaryl groups having more than two six-membered rings condensed directly onto one another and particularly preferably contains absolutely no six-membered rings condensed directly onto one another. Preferred groups $Ar^1$ and $Ar^2$ are therefore built up from in each case one or more of the groups benzene, pyridine, pyrimidine, pyridazine, pyrazine, triazine, pyrrole, thiophene, furan, imidazole, indole, benzothiophene, benzofuran, benzimidazole, carbazole, dibenzofuran or dibenzothiophene. Particularly preferred groups Ar are built up from in each case one or more groups benzene, pyridine, pyrimidine, pyridazine, pyrazine, triazine or benzimidazole.

As described above, the compounds of the formula (1) according to the invention are characterised in that at least one group $Ar^1$ represents a heteroaryl group or in that at least one group $Ar^2$ represents an electron-deficient heteroaryl group. In a preferred embodiment, $Ar^1$, if this group stands for a heteroaryl group, is also an electron-deficient heteroaryl group.

Preferred electron-deficient heteroaryl groups $Ar^1$ and $Ar^2$ are selected from the group consisting of pyridine, pyrimidine, pyrazine, pyridazine, imidazole, triazole, oxadiazole or benzimidazole, which is bonded to $L^1$ and $L^2$ respectively via any desired position and which may be substituted by one or more radicals $R^1$. Particularly preferably, electron-deficient heteroaryl groups $Ar^1$ and $Ar^2$ are selected from the group consisting of pyridine, pyrimidine, triazine or benzimidazole, each of which is bonded to $L^1$ and $L^2$ respectively via any desired position and which may be substituted by one or more radicals $R^1$.

In a preferred embodiment of the invention, the unit A-A is selected from the structures of the formula (2) or (3), in particular of the formula (2).

In a further preferred embodiment of the invention, the index n=1, 2, 3 or 4, particularly preferably 1, 2 or 3, very particularly preferably 1 or 2.

In a further preferred embodiment of the invention, the radical $R^1$ is selected, identically or differently on each occurrence, from the group consisting of H, D, F, CN, $N(R^3)_2$, a straight-chain alkyl or alkoxy group having 1 to 20 C atoms or a branched or cyclic alkyl or alkoxy group having 3 to 20 C atoms or an alkenyl group having 2 to 20 C atoms, each of which may be substituted by one or more radicals $R^3$, where one or more non-adjacent $CH_2$ groups may be replaced by $R^3C$=$CR^3$ or O and where one or more H atoms may be replaced by D or F, an aromatic or heteroaromatic ring system having 5 to 30 aromatic ring atoms, which may in each case be substituted by one or more radicals $R^3$, an aryloxy or heteroaryloxy group having 5 to 30 aromatic ring atoms, which may be substituted by one or more radicals $R^3$, or a combination of these systems, where two or more adjacent substituents $R^1$ may optionally form a monocyclic or polycyclic, aliphatic, aromatic or heteroaromatic ring system, which may be substituted by one or more radicals $R^3$. The radical $R^1$ is particularly preferably selected, identically or differently on each occurrence, from the group consisting of H, D, CN, F, a straight-chain alkyl group having 1 to 10 C atoms, particularly preferably having 1 to 4 C atoms, or a branched or cyclic alkyl group having 3 to 10 C atoms, particularly preferably having 3 to 6 C atoms, or an alkenyl group having 2 to 10 C atoms, particularly preferably having 2 to 4 C atoms, each of which may be substituted by one or more radicals $R^3$, where one or more H atoms may be replaced by D, an aromatic or heteroaromatic ring system having 5 to 12 aromatic ring atoms, which may in each case be substituted by one or more radicals $R^3$, or a combination of these systems, where two or more adjacent substituents $R^1$ may optionally form a monocyclic or polycyclic, aliphatic, aromatic or heteroaromatic ring system, which may be substituted by one or more radicals $R^3$.

In a further preferred embodiment of the invention, the radical $R^2$ is selected on each occurrence, identically or differently, from the group consisting of an aromatic or heteroaromatic ring system having 5 to 30 aromatic ring atoms, which may in each case be substituted by one or more radicals $R^3$; the $R^1$ and $R^2$ that are adjacent to one another in the 1,2-position may optionally form a monocyclic or polycyclic, aliphatic, aromatic or heteroaromatic ring system here, which may be substituted by one or more radicals $R^3$. In a particularly preferred embodiment of the invention, $R^2$ stands for phenyl, naphthyl, biphenyl, terphenyl or quaterphenyl, each of which may be substituted by one or more radicals $R^3$, in particular for phenyl or biphenyl, each of which may be substituted by one or more radicals $R^3$, but is preferably unsubstituted.

Particular preference is given to compounds of the above-mentioned formulae (1) or (8) to (18) in which the preferences given above apply simultaneously. Particular preference is therefore given to compounds in which $R^3$ is as defined above and furthermore:

Y is, identically or differently on each occurrence, for N—$R^2$;

$L^1$, $L^2$ is, identically or differently on each occurrence, a single bond or a divalent arylene or heteroarylene group having 5 to 10 aromatic ring atoms, which may in each case be substituted by one or more radicals $R^1$.

$L^3$ is a single bond, O, S, $NR^2$, an alkylene group having 1 to 10 C atoms, which may be substituted by one or more radicals $R^3$, or an aromatic or heteroaromatic ring system having 5 to 30 aromatic ring atoms, which may be substituted by one or more radicals $R^3$;

X is on each occurrence, identically or differently, $CR^1$ or N, where a maximum of two symbols X in each ring stand for N and the other symbols X stand, identically or differently on each occurrence, for $CR^1$;

$Ar^1$, $Ar^2$ stands, identically or differently on each occurrence, for an aromatic or heteroaromatic ring system having 5 to 24 aromatic ring atoms, particularly preferably having 5 to 18 aromatic ring atoms, where the aromatic or heteroaromatic ring system may in each case also be substituted by one or more radicals $R^1$; at least one group $Ar^1$ here is a heteroaryl group or at least one group $Ar^2$ is an electron-deficient heteroaryl group, which may be substituted by one or more radicals $R^1$;

n is 1, 2, 3 or 4, preferably 1, 2 or 3;

$R^1$ is selected, identically or differently on each occurrence, from the group consisting of H, D, F, CN, $N(R^3)_2$, a straight-chain alkyl or alkoxy group having 1 to 20 C atoms or a branched or cyclic alkyl or alkoxy group having 3 to 20 C atoms or an alkenyl group having 2 to 20 C atoms, each of which may be substituted by one or more radicals $R^3$, where one or more non-adjacent $CH_2$ groups may be replaced by $R^3C$=$CR^3$ or O and where one or more H atoms may be replaced by D or F, an aromatic or heteroaromatic ring system having 5 to 30 aromatic ring atoms, which may in each case be substituted by one or more radicals $R^3$, an aryloxy or heteroaryloxy group having 5 to 30 aromatic ring atoms, which may be substituted by one or more radicals $R^3$, or a combination of these systems, where two or more adjacent substituents $R^1$ may optionally form a monocyclic or polycyclic, aliphatic, aromatic or heteroaromatic ring system, which may be substituted by one or more radicals $R^3$;

$R^2$ is selected on each occurrence, identically or differently, from the group consisting of an aromatic or heteroaromatic ring system having 5 to 30 aromatic ring atoms, which may in each case be substituted by one or more radicals $R^3$; the $R^1$ and $R^2$ that are adjacent to one another in the 1,2-position may optionally form a monocyclic or polycyclic, aliphatic, aromatic or heteroaromatic ring system here, which may be substituted by one or more radicals $R^3$.

Very particular preference is given to compounds of the formula (1) or formula (8) to (18) in which $R^3$ is as defined above and furthermore:

Y is, identically or differently on each occurrence, for N—$R^2$;

L¹, L² is, identically or differently on each occurrence, a divalent arylene or heteroarylene group having 6 aromatic ring atoms, which may be substituted by one or more radicals R¹, but is preferably unsubstituted, in particular for 1,2-, 1,3- or 1,4-phenylene, pyridine, pyrimidine or triazine;

L³ is a single bond, O, S, NR², an alkylene group having 1 to 10 C atoms, which may be substituted by one or more radicals R³, or an aromatic or heteroaromatic ring system having 5 to 30 aromatic ring atoms, which may be substituted by one or more radicals R³;

X is on each occurrence, identically or differently, CR¹ or N, where a maximum of one symbol X and preferably no symbol X at all in each ring stand for N and the other symbols X stand, identically or differently on each occurrence, for CR¹;

Ar¹, Ar² stands, identically or differently on each occurrence, for an aryl or heteroaryl group having 5 to 13 aromatic ring atoms, which may in each case also be substituted by one or more radicals R¹ and which contains no aryl or heteroaryl groups having more than two six-membered rings condensed directly onto one another, in particular selected from the group consisting of in each case one or more of the groups benzene, pyridine, pyrimidine, pyridazine, pyrazine, triazine, pyrrole, thiophene, furan, imidazole, indole, benzothiophene, benzofuran, benzimidazole, carbazole, dibenzofuran or dibenzothiophene; at least one group Ar¹ or Ar² here is an electron-deficient heteroaryl group, which may be substituted by one or more radicals R¹, which is selected from the group consisting of pyridine, pyrimidine, pyrazine, pyridazine, imidazole, triazole, oxadiazole or benzimidazole, which is bonded to L¹ or L² via any desired position and which may be substituted by one or more radicals R¹;

n is 1 or 2;

R¹ is selected, identically or differently on each occurrence, from the group consisting of H, D, CN, F, a straight-chain alkyl group having 1 to 10 C atoms, particularly preferably having 1 to 4 C atoms, or a branched or cyclic alkyl group having 3 to 10 C atoms, particularly preferably having 3 to 6 C atoms, or an alkenyl group having 2 to 10 C atoms, particularly preferably having 2 to 4 C atoms, each of which may be substituted by one or more radicals R³, where one or more H atoms may be replaced by D, an aromatic or heteroaromatic ring system having 5 to 12 aromatic ring atoms, which may in each case be substituted by one or more radicals R³, or a combination of these systems, where two or more adjacent substituents R¹ may optionally form a monocyclic or polycyclic, aliphatic, aromatic or heteroaromatic ring system, which may be substituted by one or more radicals R³;

R² is selected on each occurrence, identically or differently, from the group consisting of phenyl, naphthyl, biphenyl, terphenyl or quaterphenyl, each of which may be substituted by one or more radicals R³, in particular for phenyl or biphenyl, each of which may be substituted by one or more radicals R³, but is preferably unsubstituted.

For compounds which are processed from solution, suitable substituents are also, in particular, long alkyl groups, for example having 5 to 10 C atoms, or substituted or unsubstituted oligoarylene groups. Suitable oligoarylene groups are, for example, terphenyl, in particular meta-terphenyl or branched terphenyl, meta-quaterphenyl or branched quaterphenyl.

Examples of preferred compounds in accordance with the above-mentioned embodiments or compounds as can preferably be employed in organic electronic devices are the compounds of the following structures (1) to (50).

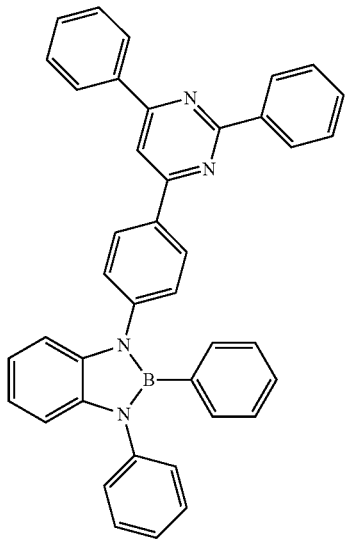

1

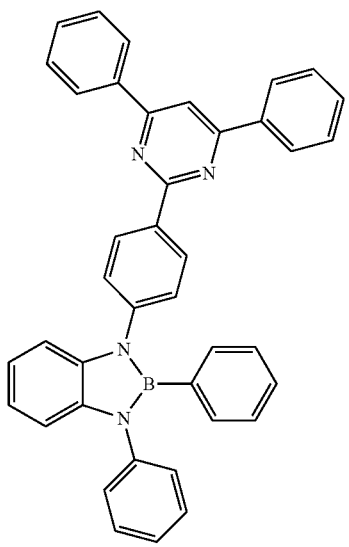

2

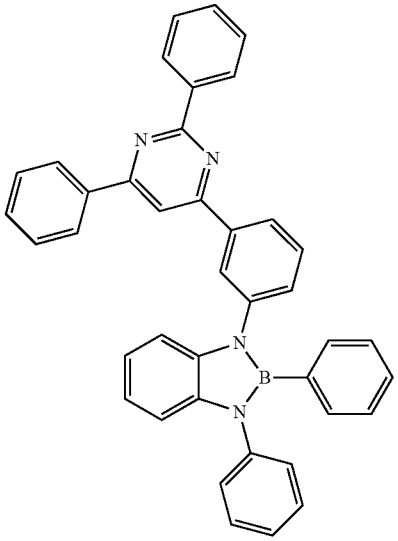

3

4
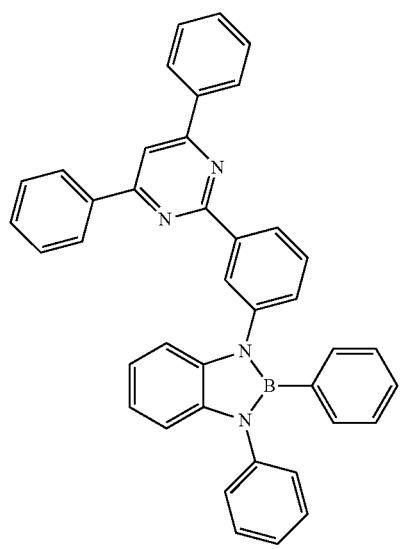
5
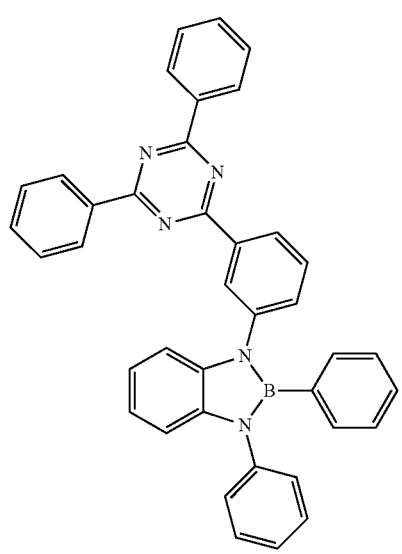
6
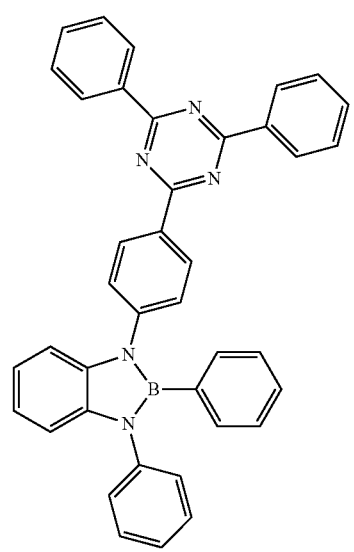
7
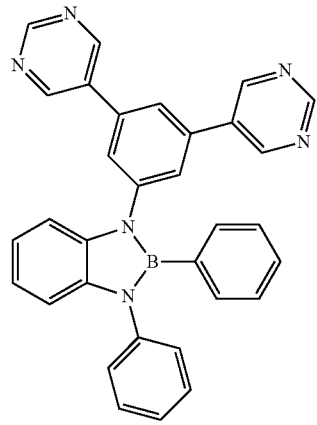
8
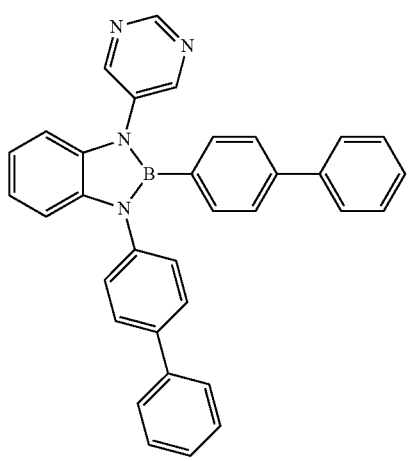
9
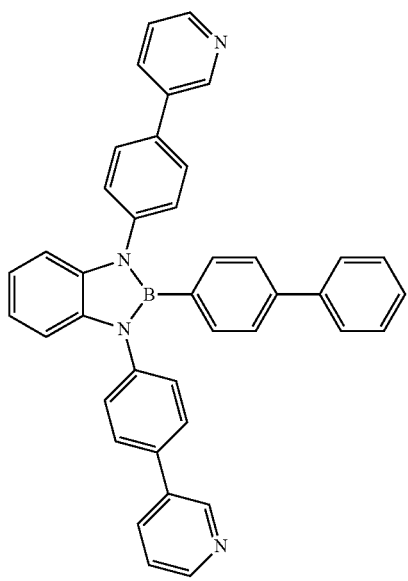

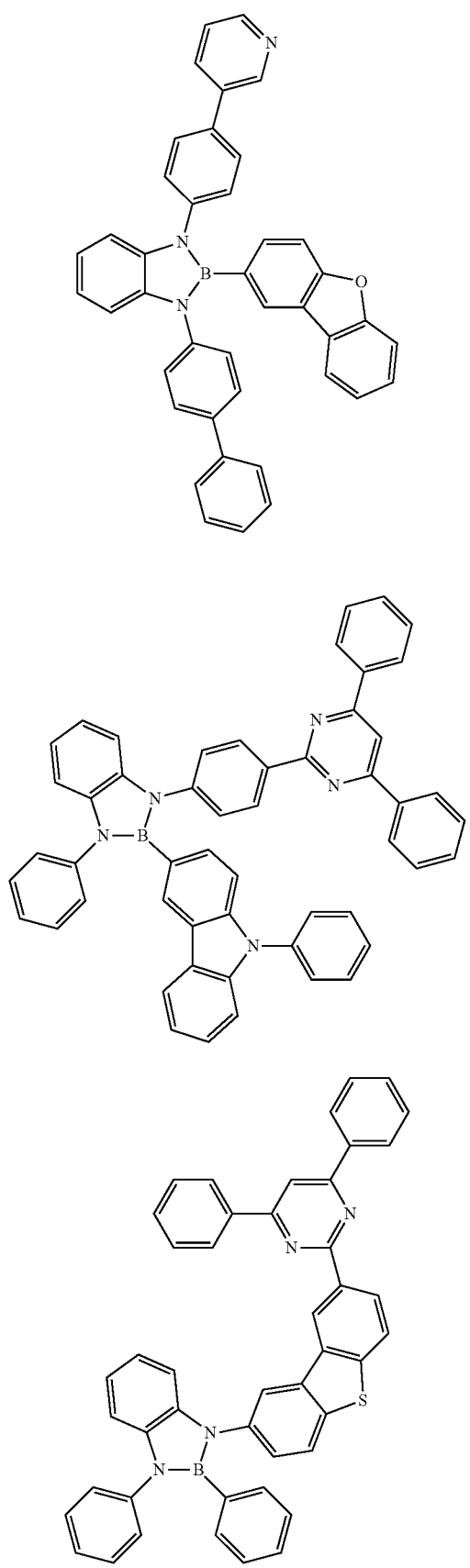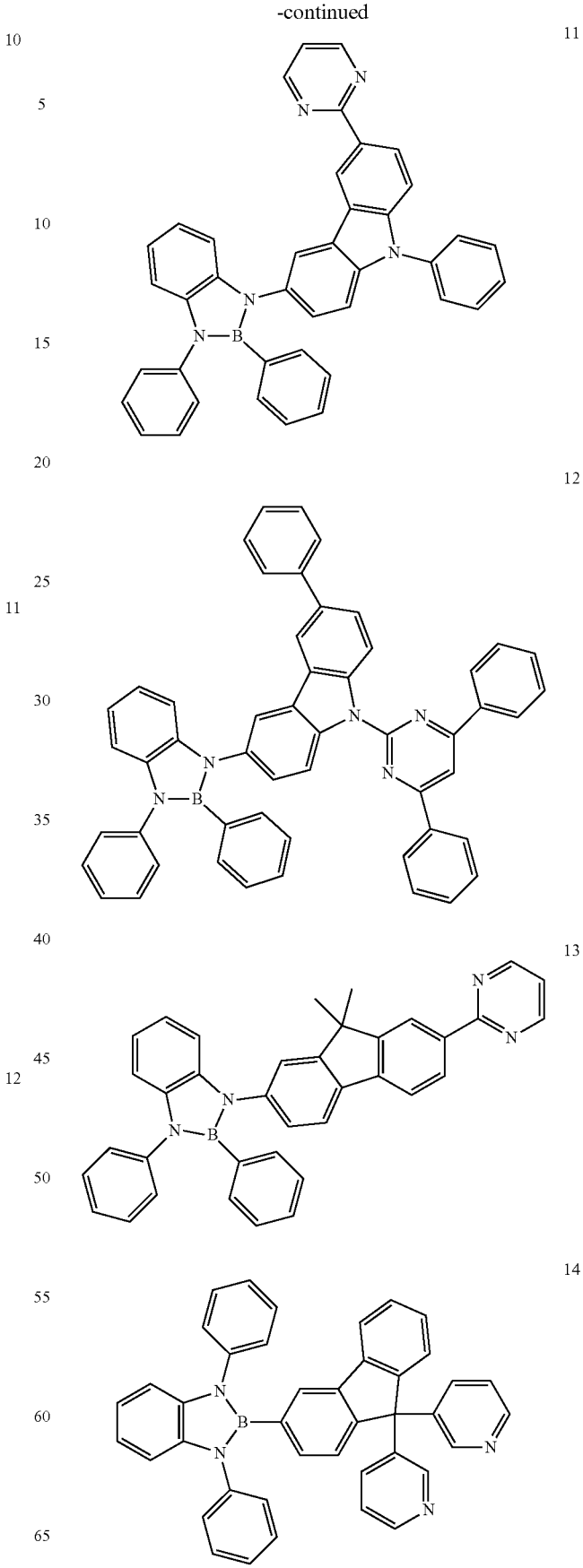

15
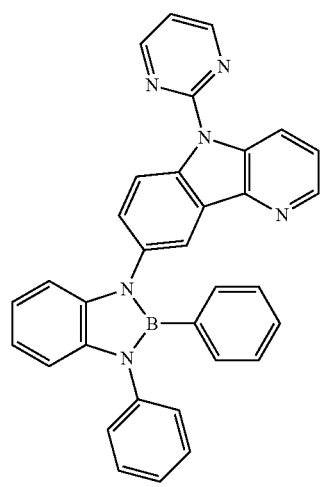
16
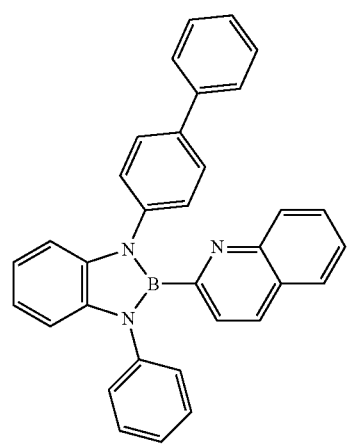
17
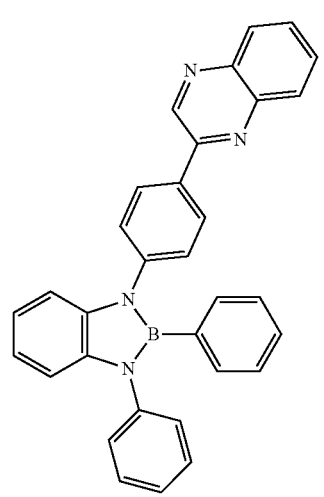
18
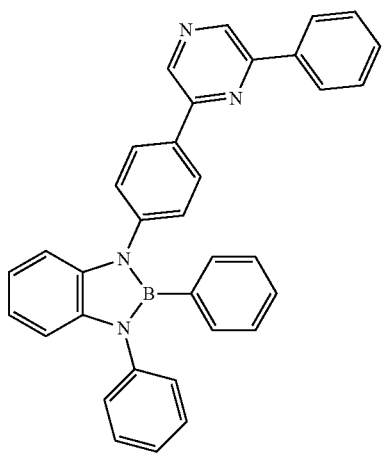
19
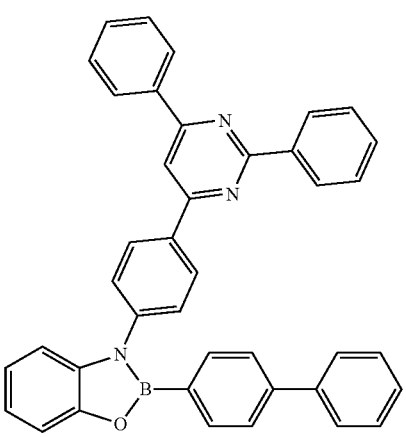
20
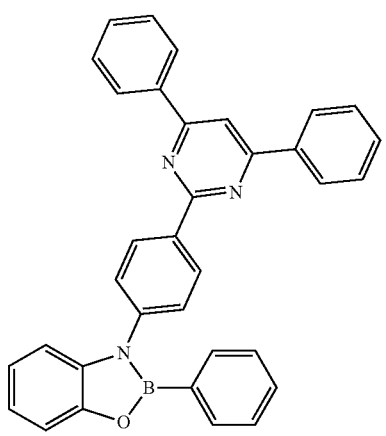

21
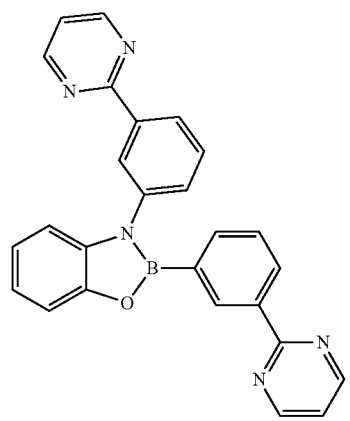
22
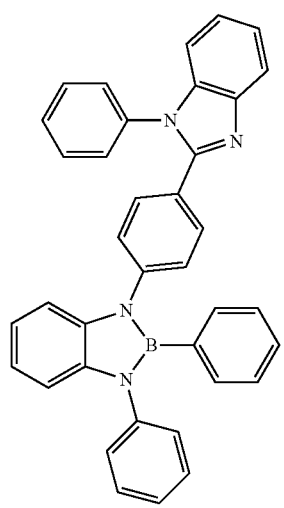
23
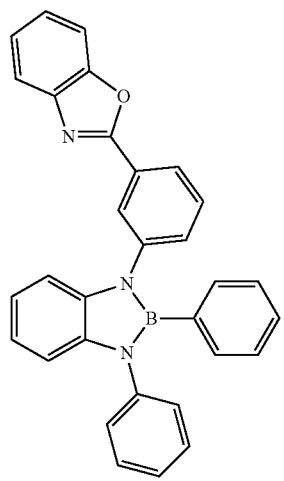
24
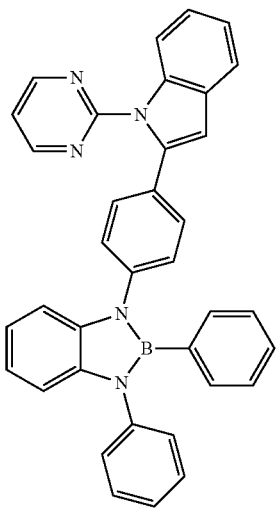
25
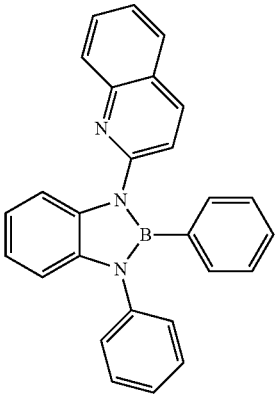
26
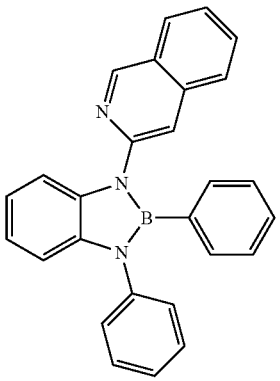

27
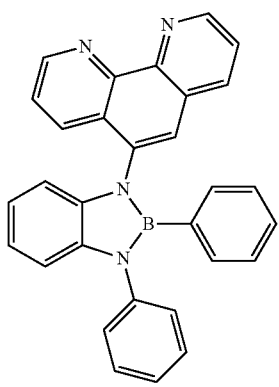
28
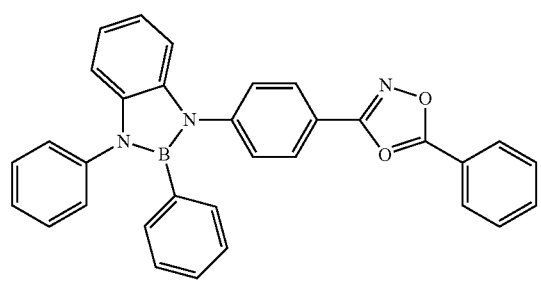
29
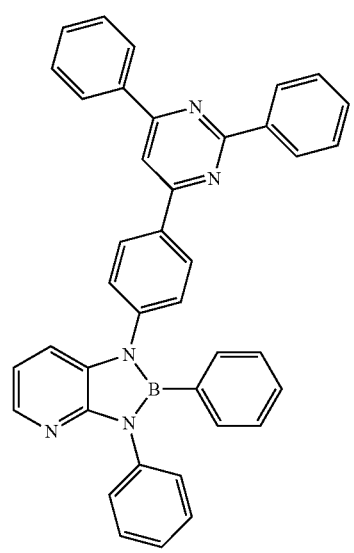
30
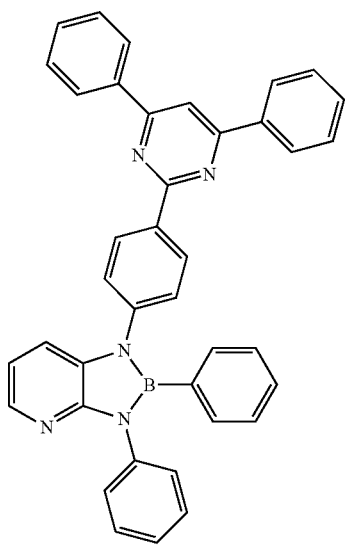
31
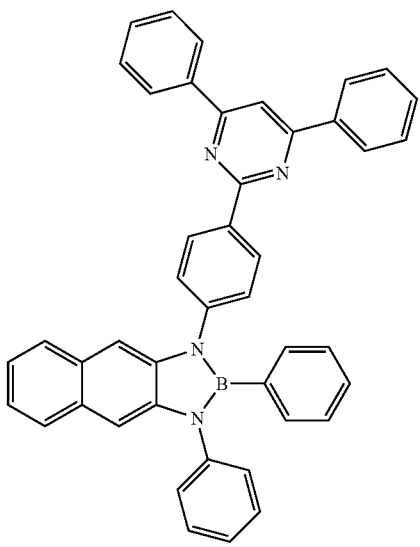
32

33
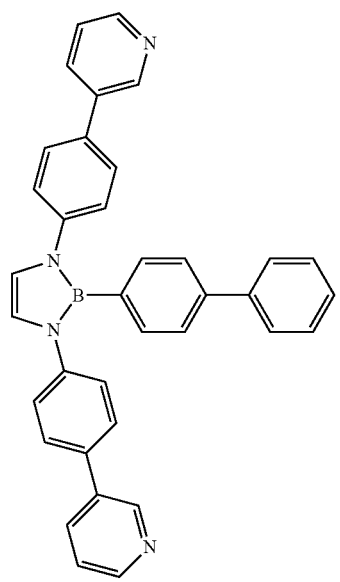
34
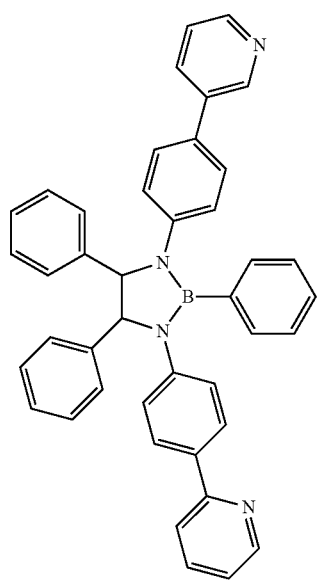
35
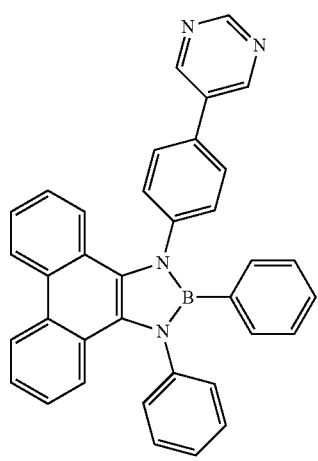
36
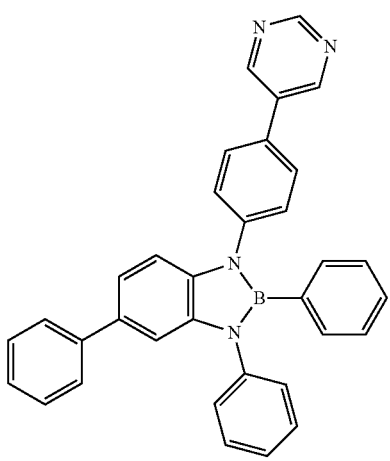
35
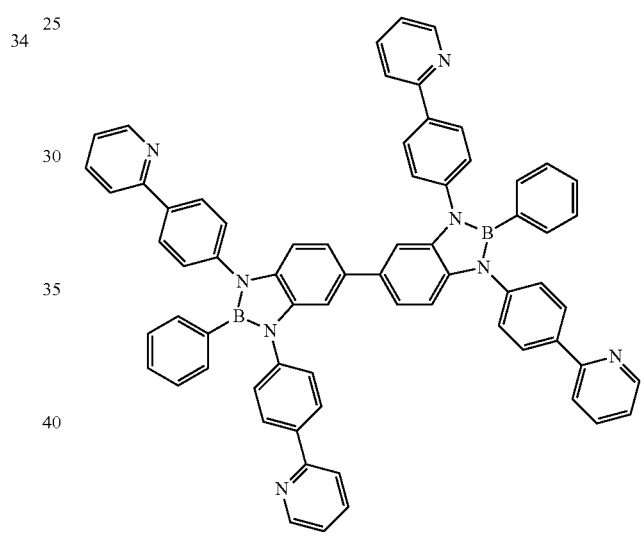
36
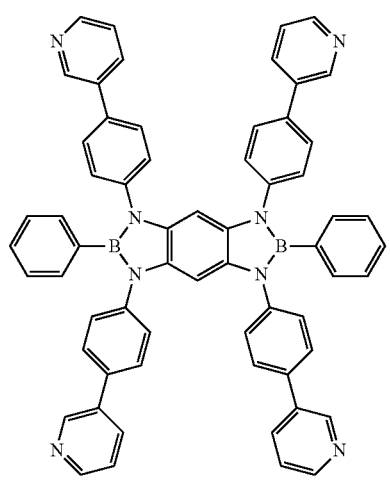

37
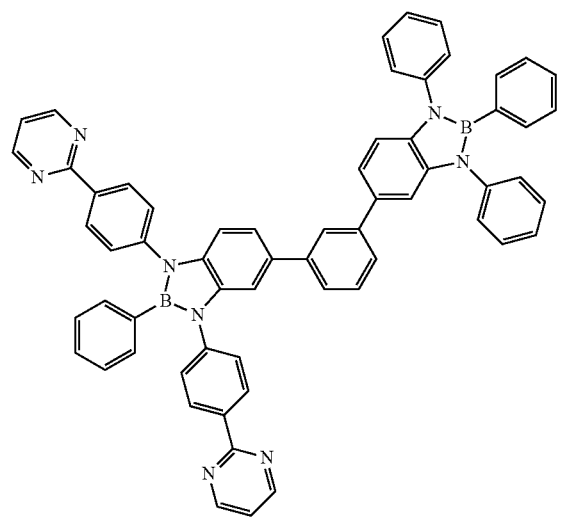
38
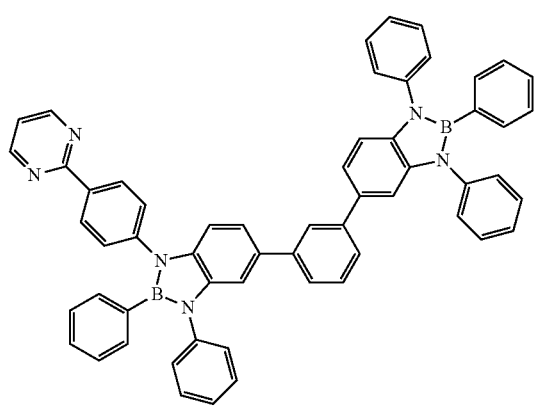
39
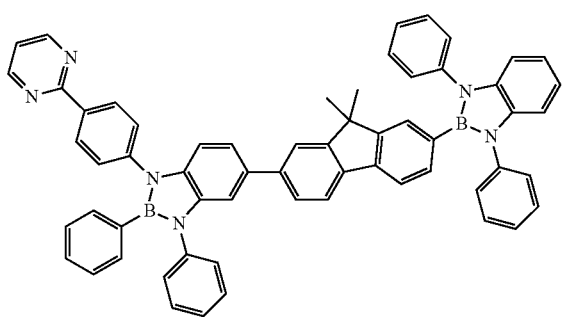
40
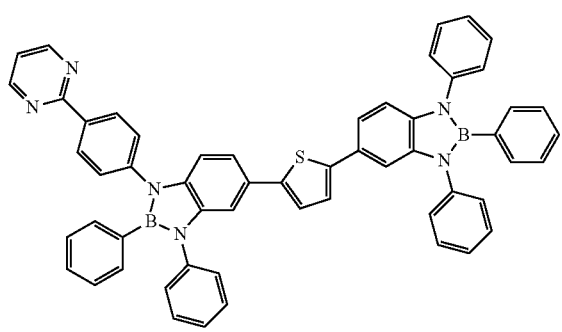
41
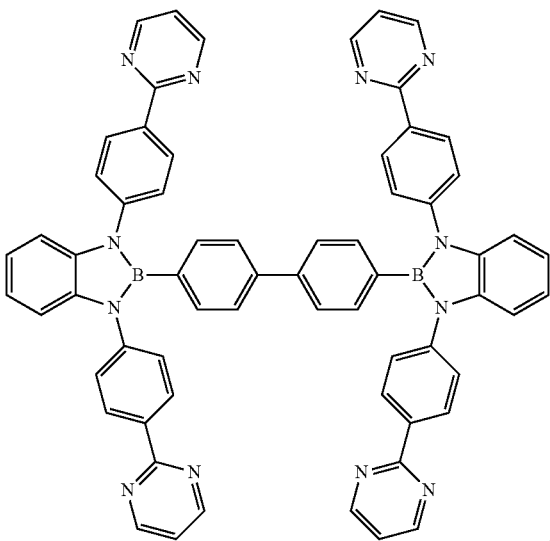
42
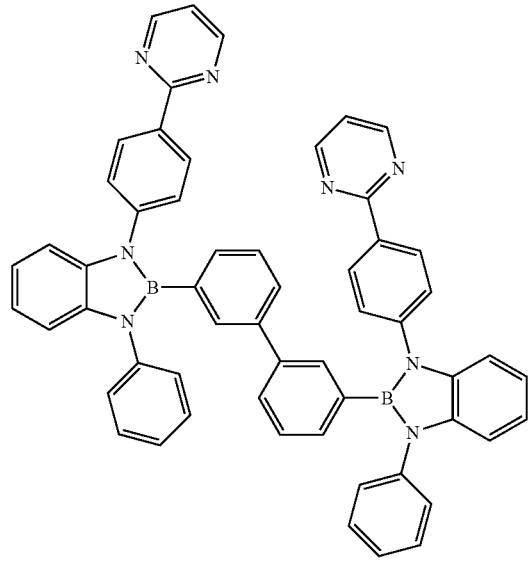
43
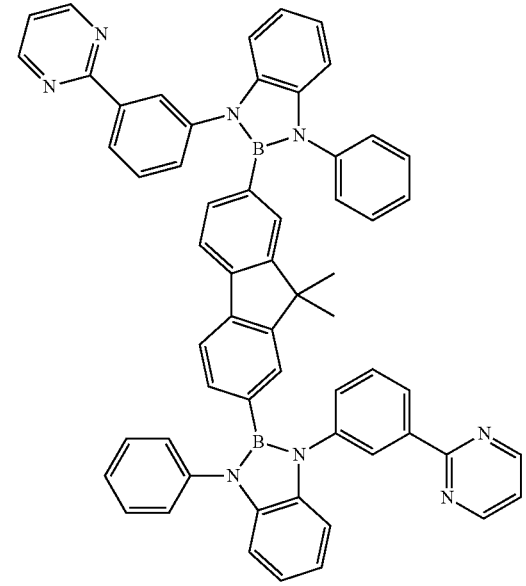

44
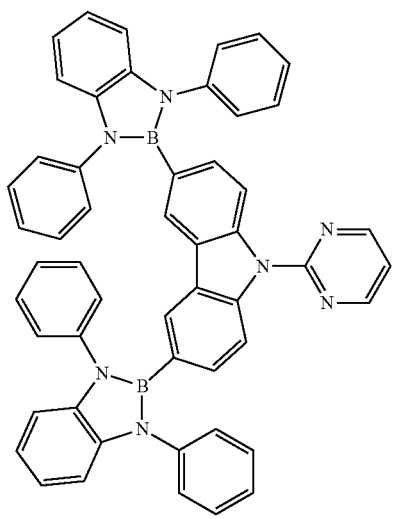
45
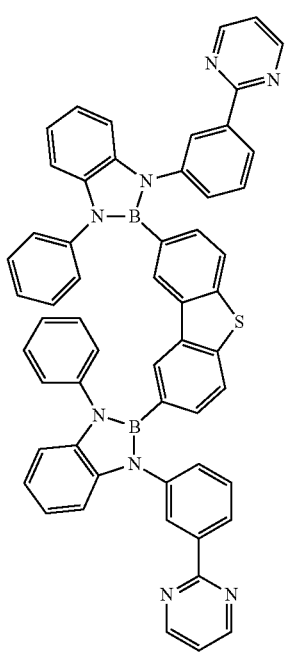
46
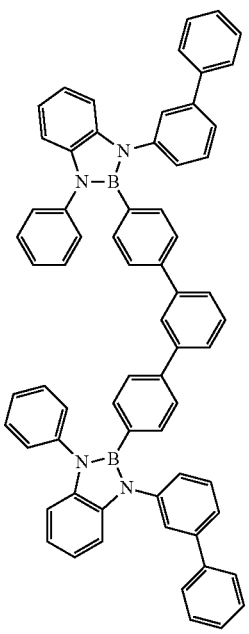
47
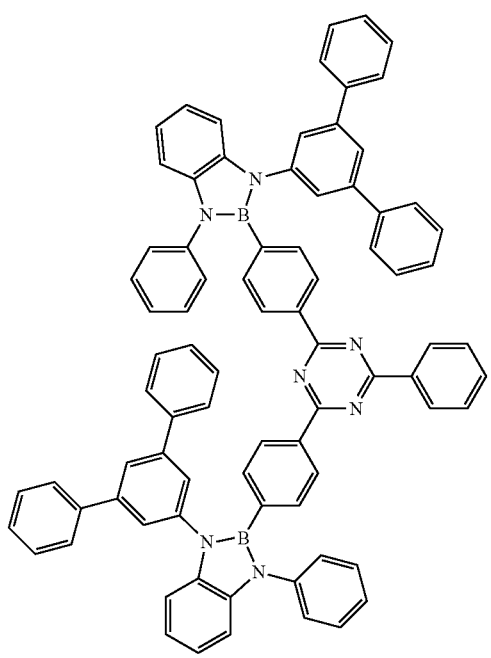

-continued

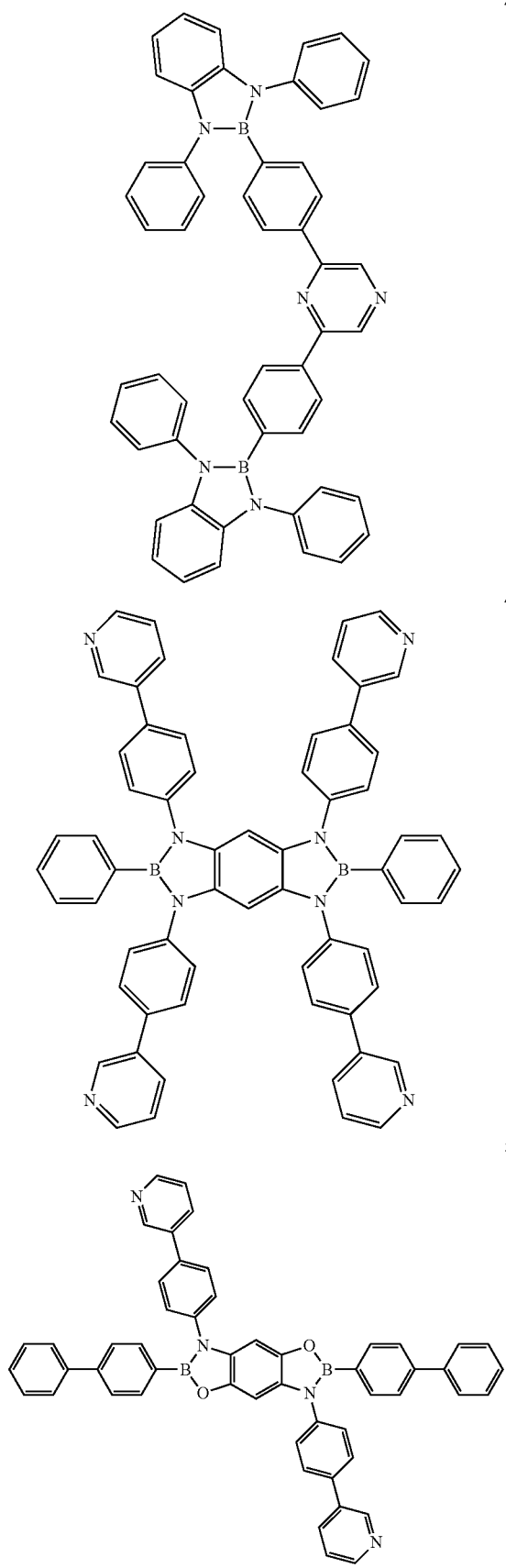

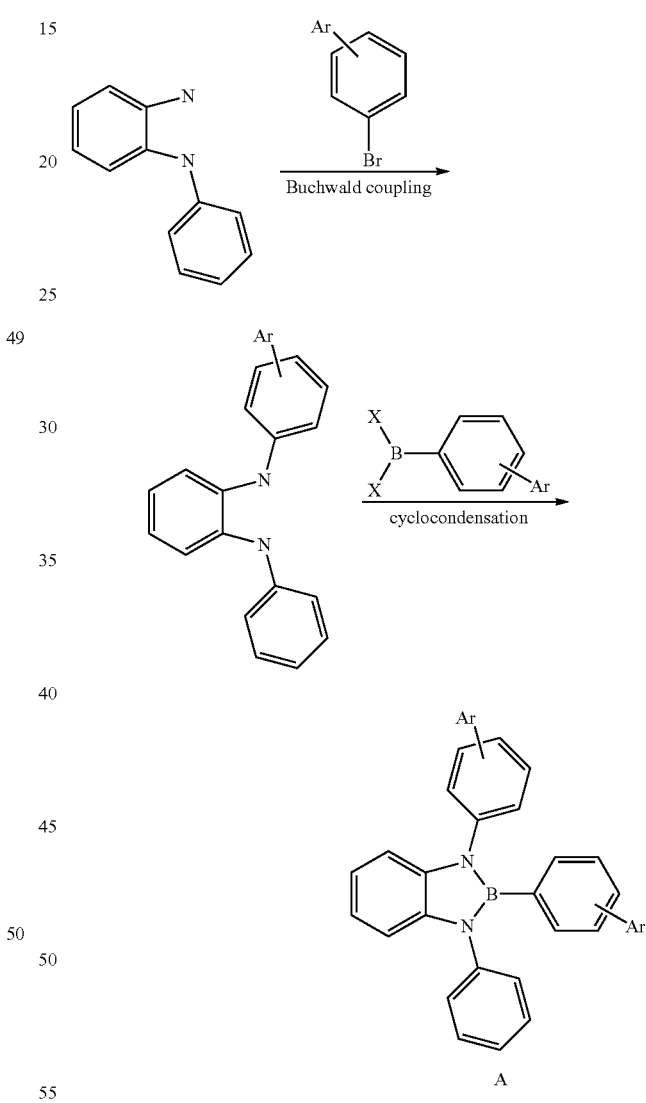

The process described below has proven particularly suitable for the preparation of the compounds of the formula (1) or the compounds according to the invention. The compounds according to the invention can be prepared by known organochemical synthesis processes. These include, for example, Hartwig-Buchwald coupling, Suzuki coupling and cyclocondensations with organoboron compounds.

The following Scheme 1 shows the synthesis of compounds A according to the invention.

For the synthesis of basic structure A, a bromoaryl is firstly coupled to N-phenylbenzene-1,2-diamine in a Buchwald reaction. The reaction of the resultant compound with boron compounds, for example borodibromobenzene, gives the corresponding diazaboroline compounds.

Scheme 2 shows the synthesis of basic structure B. It differs from the synthesis shown in Scheme 1 merely through the fact that, instead of boron dibromide compounds, 1,4-bis(dibromoborobenzene) is employed in the cyclocondensation with two equivalents of the diamine.

Scheme 2
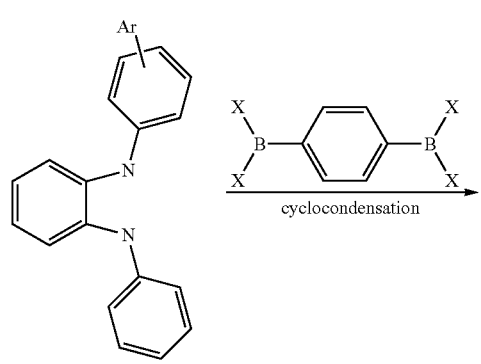
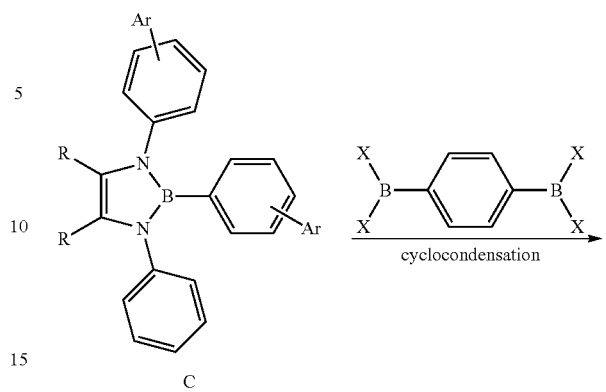
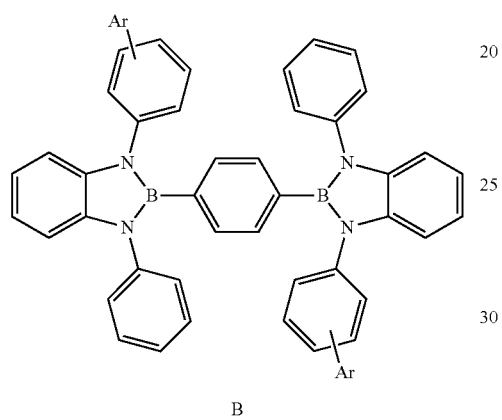
B
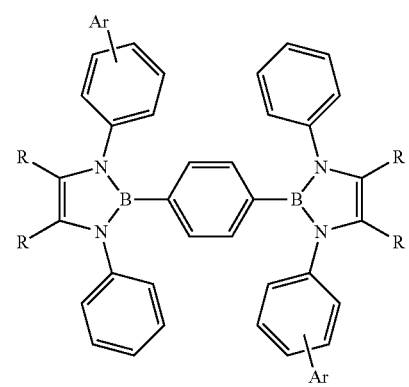
D
For basic structures C, D and E, an analogous process can be followed, as depicted in Scheme 3 and 4.
Scheme 3:
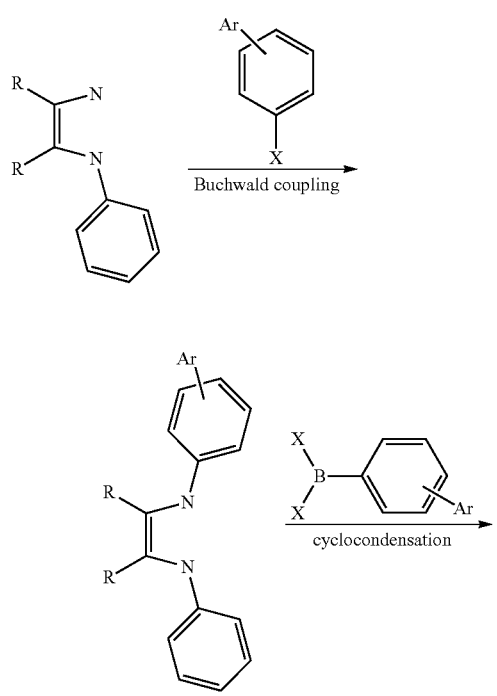
Scheme 4:
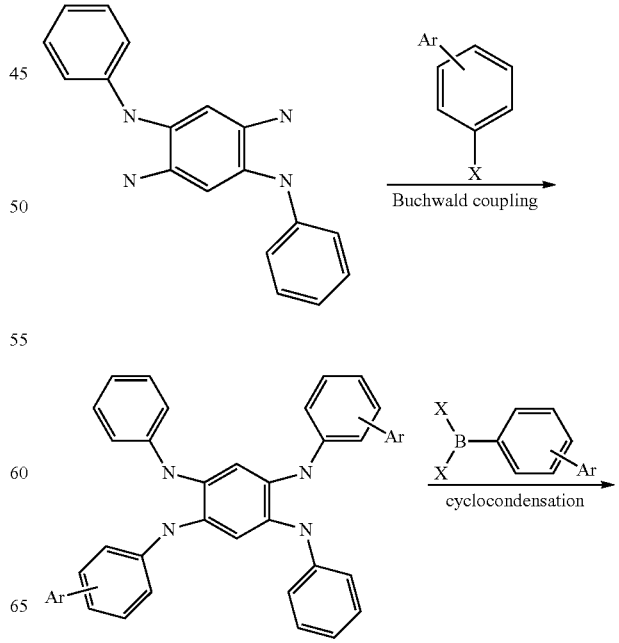

-continued

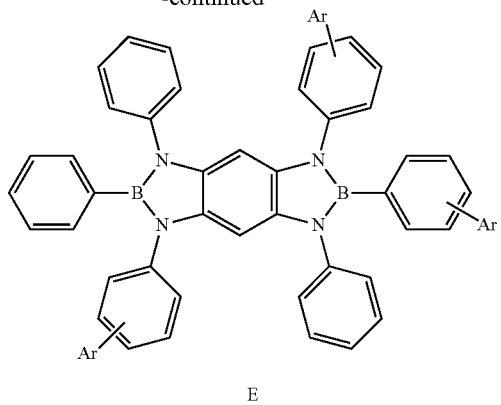

E

The synthesis routes described above are merely intended to serve as examples. The person skilled in the art will be able to fall back on alternative synthesis processes for the synthesis of the compounds according to the invention if this appears advantageous to him under the given circumstances. Furthermore, he will be able to extend and/or modify the syntheses shown utilising his general expert knowledge in the area of organic synthetic chemistry in order to prepare compounds according to the invention.

The present invention furthermore relates to a process for the preparation of the compounds according to the invention by reaction of an aromatic ortho-diamino compound with an aryl- or heteroarylboron compound in which the boron atom is substituted by two reactive leaving groups, in particular chlorine or bromine.

The present invention furthermore relates to mixtures comprising at least one compound according to the invention and at least one further compound. The further compound can be, for example, a fluorescent or phosphorescent dopant if the compound according to the invention is used as matrix material, in particular a phosphorescent dopant. Suitable dopants are mentioned below in connection with the organic electroluminescent devices and are also preferred for the mixtures according to the invention.

For processing from solution or from the liquid phase, for example by spin coating or by printing processes, solutions or formulations of the compounds or mixtures according to the invention are necessary. It may be preferred to use mixtures of two or more solvents. Suitable and preferred solvents are, for example, toluene, anisole, o-, m- or p-xylene, methyl benzoate, dimethyl anisole, mesitylene, tetralin, veratrol, THF, methyl-THF, THP, chlorobenzene, dioxane or mixtures of these solvents.

The present invention therefore furthermore relates to a formulation, in particular a solution, a suspension or a miniemulsion, comprising at least one compound or mixture according to the invention and one or more solvents, in particular organic solvents. The way in which solutions of this type can be prepared is known to the person skilled in the art and is described, for example, in WO 2002/072714, WO 2003/019694 and the literature cited therein.

The compounds and mixtures according to the invention are suitable for use in an electronic device. An electronic device here is taken to mean a device which comprises at least one layer which comprises at least one organic compound. However, the component here may also comprise inorganic materials or also layers built up entirely from inorganic materials.

The present invention therefore furthermore relates to the use of the compounds or mixtures according to the invention in an electronic device, in particular in an organic electroluminescent device.

The present invention again furthermore relates to an electronic device comprising at least one of the compounds or mixtures according to the invention mentioned above. The preferences stated above for the compound also apply to the electronic devices.

The electronic device is preferably selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitised solar cells, organic optical detectors, organic photoreceptors, organic field-quench devices (O-FQDs), light-emitting electrochemical cells (LECs), organic laser diodes (O-lasers) and "organic plasmon emitting devices" (D. M. Koller et al., Nature Photonics 2008, 1-4), preferably organic electroluminescent devices (OLEDs, PLEDs), in particular phosphorescent OLEDs.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. It is likewise possible for interlayers, which have, for example, an exciton-blocking function, to be introduced between two emitting layers. However, it should be pointed out that each of these layers does not necessarily have to be present. The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013). These can be fluorescent or phosphorescent emission layers or hybrid systems, in which fluorescent and phosphorescent emission layers are combined with one another.

The compound according to the invention in accordance with the embodiments indicated above can be employed in various layers, depending on the precise structure. Preference is given to an organic electroluminescent device comprising a compound of the formula (1) or in accordance with the preferred embodiments as matrix material for fluorescent or phosphorescent emitters, in particular for phosphorescent emitters, and/or in an electron-transport layer and/or in an electron-blocking or exciton-blocking layer and/or in a hole-transport layer, depending on the precise substitution. The preferred embodiments indicated above also apply to the use of the materials in organic electronic devices.

In a preferred embodiment of the invention, the compound of the formula (1) or in accordance with the preferred embodiments is employed as matrix material for a fluorescent or phosphorescent compound, in particular for a phosphorescent compound, in an emitting layer. The organic electroluminescent device here may comprise one emitting layer or a plurality of emitting layers, where at least one emitting layer comprises at least one compound according to the invention as matrix material.

If the compound of the formula (1) or in accordance with the preferred embodiments is employed as matrix material for an emitting compound in an emitting layer, it is preferably employed in combination with one or more phosphorescent materials (triplet emitters). Phosphorescence in the sense of this invention is taken to mean the luminescence from an excited state having spin multiplicity >1, in particular from an excited triplet state. For the purposes of this application, all luminescent transition-metal complexes and luminescent lanthanide complexes, in particular all iridium, platinum and copper complexes, are to be regarded as phosphorescent compounds.

The mixture comprising the compound of the formula (1) or in accordance with the preferred embodiments and the emitting compound comprises between 99 and 1% by vol., preferably between 98 and 10% by vol., particularly preferably between 97 and 60% by vol., in particular between 95 and 80% by vol., of the compound of the formula (1) or in accordance with the preferred embodiments, based on the entire mixture comprising emitter and matrix material. Correspondingly, the mixture comprises between 1 and 99% by vol., preferably between 2 and 90% by vol., particularly preferably between 3 and 40% by vol., in particular between 5 and 20% by vol., of the emitter, based on the entire mixture comprising emitter and matrix material.

A further preferred embodiment of the present invention is the use of the compound of the formula (1) or in accordance with the preferred embodiments as matrix material for a phosphorescent emitter in combination with a further matrix material. Particularly suitable matrix materials which can be employed in combination with the compounds of the formula (1) or in accordance with the preferred embodiments are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109 and WO 2011/000455, azacarbazole derivatives, for example in accordance with EP 1617710, EP 1617711, EP 1731584, JP 2005/347160, bipolar matrix materials, for example in accordance with WO 2007/137725, silanes, for example in accordance with WO 005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, bridged carbazole derivatives, for example in accordance with US 2009/0136779, WO 2010/050778, WO 2011/042107, WO 2011/088877 or in accordance with the unpublished application EP 11003232.3, triphenylene derivatives, for example in accordance with the unpublished application DE 102010048608.6, or lactams, for example in accordance with the unpublished applications DE 102010012738.8 or DE 102010019306.2. A further phosphorescent emitter which emits at shorter wavelength than the actual emitter may likewise be present in the mixture as co-host.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescent emitters used are preferably compounds which contain copper, molybdenum, tungsten, rhenium, ruthenium, osmium, rhodium, iridium, palladium, platinum, silver, gold or europium, in particular compounds which contain iridium or platinum. For the purposes of the present invention, all luminescent compounds which contain the above-mentioned metals are regarded as phosphorescent compounds.

Examples of the emitters described above are revealed by the applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898. Furthermore suitable are the complexes in accordance with the unpublished applications EP 10006208.2 and DE 102010027317.1. In general, all phosphorescent complexes as used in accordance with the prior art for phosphorescent OLEDs and as are known to the person skilled in the art in the area of organic electroluminescence are suitable, and the person skilled in the art will be able to use further phosphorescent complexes without inventive step.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is identical or similar to the metal complex in the emitting layer as hole-transport or hole-injection material directly adjacent to the emitting layer, as described, for example, in WO 2009/030981.

It is furthermore possible to employ the compounds according to the invention in an electron-transport layer and/or in a hole-blocking layer.

In the further layers of the organic electroluminescent device according to the invention, it is possible to use all materials as usually employed in accordance with the prior art. The person skilled in the art can therefore, without inventive step, all materials known for organic electroluminescent devices in combination with the compounds of the formula (1) according to the invention or in accordance with the preferred embodiments.

Preference is furthermore given to an organic electroluminescent device, characterised in that one or more layers are applied by means of a sublimation process, in which the materials are vapour-deposited in vacuum sublimation units at an initial pressure of less than $10^{-5}$ mbar, preferably less than $10^{-6}$ mbar. However, it is also possible for the initial pressure to be even lower or higher, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, ink-jet printing, LITI (light induced thermal imaging, thermal transfer printing), screen printing, flexographic printing, offset printing or nozzle printing. Soluble compounds, which are obtained, for example, by suitable substitution, are necessary for this purpose. These processes are also particularly suitable for oligomers, dendrimers and polymers.

Also possible are hybrid processes, in which, for example, one or more layers are applied from solution and one or more further layers are applied by vapour deposition. Thus, it is possible, for example, to apply the emitting layer from solution and to apply the electron-transport layer by vapour deposition.

These processes are generally known to the person skilled in the art and can be applied by him without inventive step to organic electroluminescent devices comprising the compounds according to the invention.

The compounds according to the invention and the organic electroluminescent devices according to the invention are distinguished over the prior art by one or more of the following surprising advantages:

1. The compounds according to the invention, employed as matrix material for fluorescent or phosphorescent emitters, result in very high efficiencies and/or in long lifetimes. This applies, in particular, if the compounds are employed as matrix material for a phosphorescent emitter. Significantly better efficiencies, in particular power efficiencies, and lifetimes are obtained here than on use of structurally similar boronic acid derivatives as matrix materials.
2. The compounds according to the invention are suitable not only as matrix for green- and red-phosphorescent compounds, but also, depending on the structure, for blue-phosphorescent compounds.
3. The compounds according to the invention have high thermal stability.
4. The compounds according to the invention, employed in organic electroluminescent devices, result in high efficiencies and in steep current/voltage curves with low use voltages.

These above-mentioned advantages are not accompanied by an impairment of the other electronic properties.

The invention is explained in greater detail by the following examples without wishing to restrict it thereby. The person skilled in the art will be able to carry out the invention throughout the range disclosed from the descriptions and prepare further complexes according to the invention without inventive step and use them in electronic devices or use the process according to the invention.

EXAMPLES

The following syntheses are, unless indicated otherwise, carried out under a protective-gas atmosphere in dried solvents. The solvents and reagents can be purchased from ALDRICH or ABCR. The figures in square brackets in each case represent the CAS numbers of the starting materials that are known from the literature.

Example 1: 1-[4-(4,6-Diphenylpyrimidin-2-yl)phenyl]-2,3-diphenyl-2,3-dihydro-1H-benzo-1,3,2-diazaborole a) 2-(4-Bromophenyl)-4,6-diphenylpyrimidine

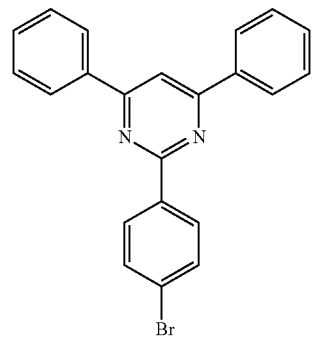 [SMILES: Brc1ccc(-c2nc(-c3ccccc3)cc(-c3ccccc3)n2)cc1]

10.0 g (53.8 mmol) of 4-bromobenzonitrile and 11.5 g (200 mmol) of hydroxylammonium chloride are dissolved in 400 ml of methanol at room temperature with stirring. 14.9 g (17.8 mmol) of sodium hydrogensulfate and 60 ml of DI water are subsequently added. The reaction mixture is boiled under reflux for 3 h. The yellow reaction solution is concentrated under reduced pressure. The residue remaining is recrystallised from methanol. The yield is 11.0 g of 4-bromo-N-hydroxybenzamidine (76% of theory).

53.2 g (0.3 mol) of 4-bromo-N-hydroxybenzamidine, 42.7 g (0.2 mol) of benzylideneacetophenone and 0.6 ml (10.0 mmol) of glacial acetic acid are suspended and stirred at room temperature for 30 min. The batch is subsequently stirred at 150° C. for 24 h. The residue formed is washed with toluene and purified by means of preparative silica-gel chromatography. Yield: 35.0 g (42.4% of theory).

b) (4,6-Diphenylpyrimidin-2-yl)phenyl]-N'-phenyl-1,2-diaminobenzene

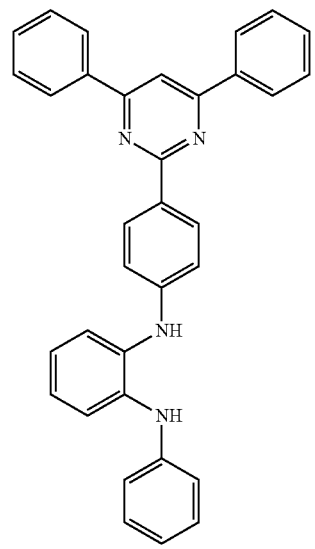 [SMILES: c1ccc(Nc2ccccc2Nc2ccc(-c3nc(-c4ccccc4)cc(-c4ccccc4)n3)cc2)cc1]

20.0 g (108.5 mmol) of N-phenyl-1,2-diaminobenzene, 44.0 g (0.11 mol) of 2-(4-bromophenyl)-4,6-diphenylpyrimidine, 4.4 g (5.4 mmol) of 1,1-bis(di-phenylphosphino)

ferrocenepalladium(II) dichloride complex with dichloromethane and 32.2 g (325 mmol) of sodium tert-butoxide are heated at the boil for 5 h in 300 ml of toluene under protective atmosphere. The mixture is subsequently partitioned between toluene and water, the organic phase is washed three times with water and dried over Na$_2$SO$_4$ and evaporated in a rotary evaporator. The residue remaining is recrystallised from heptane/toluene. The yield is 25.0 g (42% of theory).

c) 4-(4,6-Diphenylpyrimidin-2-yl)phenyl]-2,3-diphenyl-2,3-dihydro-1H-benzo-1,3,2-diazaborole

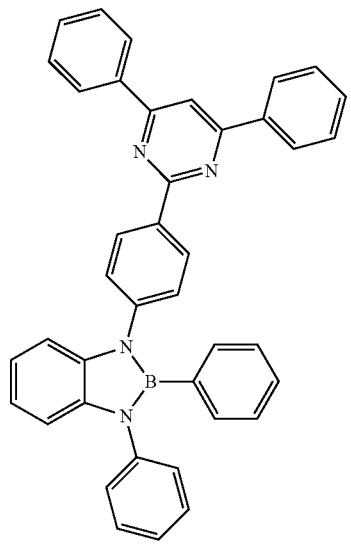 [SMILES: c1ccc(B2N(c3ccccc3)c3ccccc3N2c2ccc(-c3nc(-c4ccccc4)cc(-c4ccccc4)n3)cc2)cc1]

9.3 g (61 mmol) of trimethylphenylsilane are dissolved in 250 ml of toluene at room temperature with stirring. 11.4 ml (118 mmol) of boron tribromide are subsequently slowly added dropwise, and the brownish solution is heated under reflux for 2 h. When the reaction is complete, 150 ml of dried toluene are added, and about 300 ml of toluene are distilled off via a water separator in order to remove the excess amount of BBr$_3$. The batch is then concentrated to about 60 ml of toluene and stored under protective gas.

27.0 g (55.0 mmol) of (4,6-diphenylpyrimidin-2-yl)phenyl]-N'-phenyl-1,2-diaminobenzene are dissolved in 500 ml of toluene, 31.0 ml (220.1 mmol) of triethylamine are added, and the mixture is subsequently cooled to 0° C. 61 ml (61 mmol) of a 1M solution of dibromo(phenyl)borane in toluene are slowly added dropwise to the reaction mixture at 0° C. with stirring. The reaction mixture is warmed to room temperature over a period of 30 min. After cooling of the reaction mixture, 600 ml of EtOH are added dropwise. The precipitated solid is recrystallised from toluene and subsequently sublimed 28.4 g (89.6% of theory, purity >99.9%)

Example 2: 3-[4-(2,6-Diphenylpyrimidin-4-yl)phenyl]-1,2-diphenyl-1,3,2-benzodiazaborole a) 4-(4-Bromophenyl)-2,6-diphenylpyrimidine

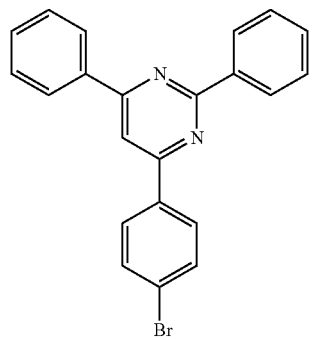 [SMILES: Brc1ccc(-c2cc(-c3ccccc3)nc(-c3ccccc3)n2)cc1]

107.7 g (0.5 mol) of 4-bromoacetophenone and 50.0 ml (0.5 mol) of benz-aldehyde are initially introduced, and 815 ml of sodium hydroxide solution (2 mol/l, 1.6 mol) and 850 ml of DI water are added. The reaction mixture is stirred at 40° C. for 24 h. The precipitated solid is filtered off with suction and rinsed with DI water. The crude product obtained in this way is recrystallised from ethanol. Yield 113 g (80% of theory).

21.8 g (0.4 mol) of KOH pellets are dissolved in 500 ml of EtOH. 38.0 g (0.2 mol) of benzamidine hydrochloride and 115.0 g (0.4 mol) of (E)-1-(4-bromophenyl)-3-phenylprop-2-en-1-one, in each case dissolved in 250 ml of ethanol, are subsequently added, and the mixture is heated under reflux for 3 h. After cooling to room temperature, the precipitated solid is filtered off with suction, washed a number of times with ethanol and dried. Yield: 76.0 g (81% of theory).

b) 3-[4-(2,6-Diphenylpyrimidin-4-yl)phenyl]-1,2-diphenyl-1,3,2-benzodiazaborole

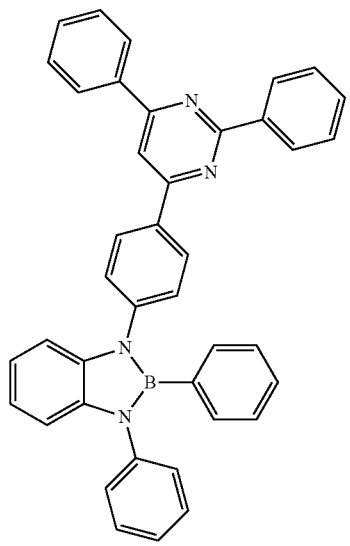 [SMILES: c1ccc(B2N(c3ccccc3)c3ccccc3N2c2ccc(-c3cc(-c4ccccc4)nc(-c4ccccc4)n3)cc2)cc1]

14.3 g of N-phenyl-1,2-diaminobenzene (77.5 mmol), 30.0 g (77.5 mol) of 4-(4-bromophenyl)-2,6-diphenylpyrimidine, 3.2 g (3.9 mmol) of 1,1-bis-(diphenylphosphino)ferrocenepalladium(II) dichloride complex with dichloromethane, and 23 g of sodium tert-butoxide (232 mmol) are heated at the boil for 5 h in 300 ml of toluene under protective atmosphere. The mixture is subsequently partitioned between toluene and water, the organic phase is washed three times with water and dried over Na₂SO₄ and evaporated in a rotary evaporator. The residue remaining is recrystallised from heptane/toluene. The yield is 27.0 g (71% of theory).

23.6 g (48.0 mmol) of the diaminobenzene derivative are dissolved in 500 ml of toluene, 27.1 ml (192 mmol) of triethylamine are added, and the mixture is subsequently cooled to 0° C. 50 ml of a 1M solution of dibromo-(phenyl)borane (50 mmol) in toluene are slowly added dropwise to the reaction mixture at 0° C. with stirring. The reaction mixture is warmed to room temperature over a period of 30 min. After cooling of the reaction mixture, 600 ml of ethanol are added dropwise. The precipitated solid is recrystallised from toluene and subsequently sublimed. Yield: 20.2 g (73% of theory, purity >99.9%).

Example 3: 2-Biphenyl-4-yl-3-[4-(4,6-diphenylpyrimidin-2-yl)phenyl]-2,3-dihydrobenzo-1,3,2-oxazaborole a) 2-[4-(4,6-Diphenylpyrimidin-2-yl)phenylamino]phenol

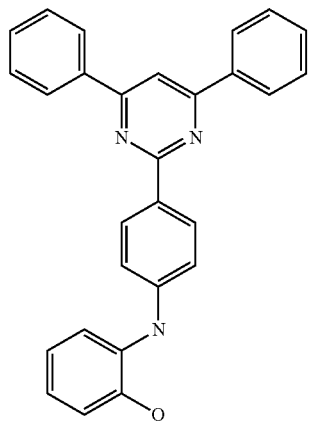 [SMILES: Oc1ccccc1Nc1ccc(-c2nc(-c3ccccc3)cc(-c3ccccc3)n2)cc1]

10.0 g of 2-aminophenol (137 mmol), 53 g (137 mmol) of 2-(4-bromophenyl)-4,6-diphenylpyrimidine, 5.3 g (27.4 mmol) of CuI and 89 g (274 mmol) of Cs₂CO₃ are heated at the boil for 5 h in 300 ml of DMF under protective atmosphere. The mixture is subsequently partitioned between ethyl acetate and water, the organic phase is washed three times with water and dried over Na₂SO₄ and evaporated in a rotary evaporator. The residue remaining is recrystallised from heptane/toluene. The yield is 39.9 g (70% of theory).

b) 2-Biphenyl-4-yl-3-[4-(4,6-diphenylpyrimidin-2-yl)phenyl]-2,3-dihydrobenzo-1,3,2-oxazaborole

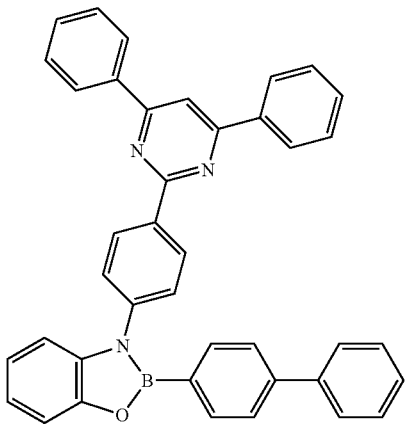 [SMILES: c1ccc(-c2ccc(B3Oc4ccccc4N3c3ccc(-c4nc(-c5ccccc5)cc(-c5ccccc5)n4)cc3)cc2)cc1]

25.6 g (62.0 mmol) of the aminobenzene derivative are dissolved in 500 ml of toluene, 26 ml (185 mmol) of triethylamine are added, and the mixture is subsequently cooled to 0° C. 62 ml of a 1M solution of dibromo-(4-biphenyl)borane (62 mmol) in toluene are slowly added dropwise to the reaction mixture at 0° C. with stirring. The reaction mixture is warmed to room temperature over a period of 30 min. After cooling of the reaction mixture, 600 ml of ethanol are added dropwise. The precipitated solid is recrystallised from toluene and subsequently sublimed. Yield: 17.8 g (50% of theory, purity >99.9%).

Example 4: 3,3'-Bis-(1-phenyl-3-(4-pyrimidin-2-ylphenyl)-2,3-dihydro-1H-benzo-1,3,2-diazaborol-2-yl)biphenyl

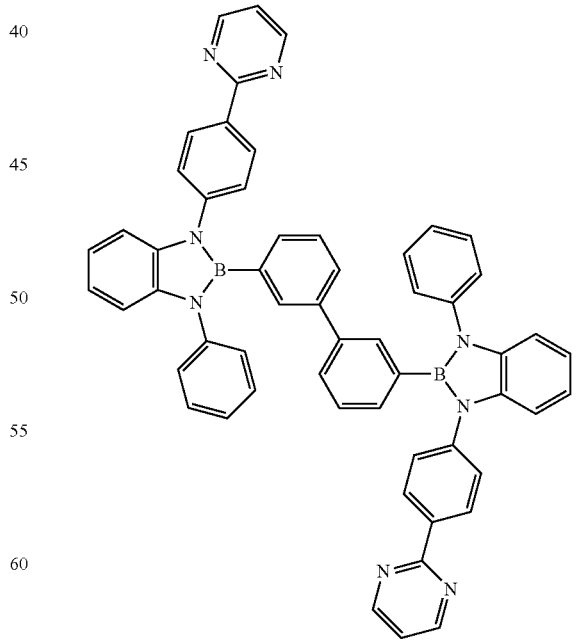

40.0 g (217 mmol) of N-phenyl-1,2-diaminobenzene, 51 g (217 mmol) of 2-(4-bromophenyl)pyrimidine, 8.8 g (10.9 mmol) of 1,1-bis(diphenyl-phosphino)ferrocenepalladium (II) dichloride complex with dichloromethane, and 64.5 g of sodium tert-butoxide (651 mmol) are heated at the boil for 8 h in 600 ml of toluene under protective atmosphere. The mixture is subsequently partitioned between toluene and water, the organic phase is washed three times with water and dried over Na$_2$SO$_4$ and evaporated in a rotary evaporator. The residue remaining is recrystallised from heptane/toluene. The yield is 44.1 g (60% of theory).

30 g (89.0 mmol) of (2-pyrimidinyl)phenyl]-N'-phenyl-1,2-diaminobenzene are dissolved in 600 ml of toluene, 62 ml (443 mmol) of triethylamine are added, and the mixture is subsequently cooled to 0° C. 45 ml of a 1M solution of bis(dibromo-(3,3'-diphenyl)borane) (45 mmol) in toluene are slowly added dropwise to the reaction mixture at 0° C. with stirring. The reaction mixture is warmed to room temperature over a period of 30 min. After cooling of the reaction mixture, 600 ml of ethanol are added dropwise. The precipitated solid is recrystallised from toluene and subsequently sublimed. Yield: 37 g (70% of theory, purity >99.9%)

Example 5: 1-[4-(4,6-Diphenylpyrimidin-2-yl)phenyl]-2,3-diphenyl-2,3-dihydro-1H-1,3,2-diazaborolo[4,5-b]pyridine

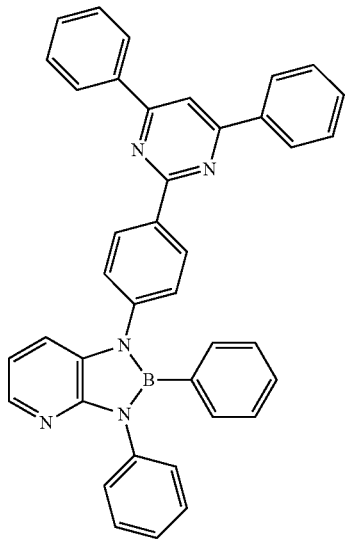 [SMILES: c1ccc(B2N(c3ccc(-c4nc(-c5ccccc5)cc(-c5ccccc5)n4)cc3)c3cccnc3N2c2ccccc2)cc1]

15.0 g (81 mmol) of N-phenylpyridine-2,3-diamine, 31.5 g (81 mmol) of 2-(4-bromophenyl)pyrimidine, 3.3 g (4 mmol) of 1,1-bis(diphenylphos-phino)ferrocenepalladium (II) dichloride complex with dichloromethane, and 23.3 g of sodium tert-butoxide (243 mmol) are heated at the boil for 8 h in 400 ml of toluene under protective atmosphere. The mixture is subsequently partitioned between toluene and water, the organic phase is washed three times with water and dried over Na$_2$SO$_4$ and evaporated in a rotary evaporator. The residue remaining is recrystallised from heptane/toluene. The yield is 17 g (45% of theory).

17 g (34.6 mmol) of the diaminopyridine derivative are dissolved in 200 ml of toluene, 19.5 ml (138 mmol) of triethylamine are added, and the mixture is subsequently cooled to 0° C. 38 ml of a 1M solution of dibromo(phenyl)borane (38 mmol) in toluene are slowly added dropwise to the reaction mixture at 0° C. with stirring. The reaction mixture is warmed to room temperature over a period of 30 min. After cooling of the reaction mixture, 200 ml of ethanol are added dropwise. The precipitated solid is recrystallised from toluene and subsequently sublimed. Yield: 12 g (60% of theory, purity >99.9%).

Example 6: 2-[4-(2,6-Diphenylpyrimidin-4-yl)phenyl]-1,3-diphenyl-2,3-dihydro-1H-benzo-1,3,2-diazaborole a) 2-Bromo-1,3-diphenyl-2,3-dihydro-1H-benzo-1,3,2-diazaborole

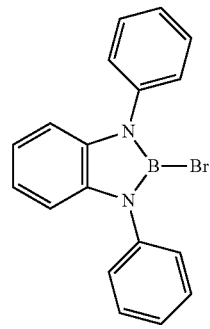 [SMILES: BrB1N(c2ccccc2)c2ccccc2N1c1ccccc1]

20.0 g (77 mmol) of N,N'-diphenylbenzene-1,2-diamine are dissolved in 300 ml of toluene, 42 ml (307 mmol) of triethylamine are added, and the mixture is subsequently cooled to 0° C. 8.14 ml (85 mmol) of boron tribromide in 20 ml of toluene are slowly added dropwise to the reaction mixture at 0° C. with stirring. The reaction mixture is warmed b room temperature over a period of 30 min. When the reaction is complete, 200 ml of dried toluene are added, and about 400 ml of toluene are distilled off via a water separator in order to remove the excess amount of BBr$_3$. The batch is then concentrated to about 100 ml and stored under protective gas.

b) 2-[4-(2,6-Diphenylpyrimidin-4-yl)phenyl]-1,3-diphenyl-2,3-dihydro-1H-benzo-1,3,2-diazaborole

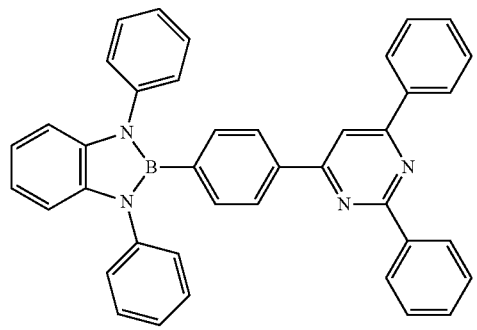 [SMILES: c1ccc(-c2cc(-c3ccc(B4N(c5ccccc5)c5ccccc5N4c4ccccc4)cc3)nc(-c3ccccc3)n2)cc1]

11.9 g (34 mmol) of 4-(4-bromophenyl)-2,6-diphenylpyrimidine are dissolved in 300 ml of THF and subsequently cooled to −100° C. 22 ml (38 mmol) of a 1.6M solution of n-butyllithium in hexane are slowly added dropwise to the reaction mixture with stirring. The reaction mixture is stirred for 30 min. 200 ml (34 mmol) of a solution of 2-bromo-1,3-diphenyl-2,3-dihydro-1H-benzo-1,3,2-diazaborole in toluene are subsequently added dropwise. The reaction mixture is warmed to 0° C. over a period of 4 h, then 600 ml of ethanol are added dropwise. The precipitated solid is recrystallised from toluene and subsequently sublimed. Yield: 11 g (60% of theory, purity >99.9%).

Example 7: Production of the OLEDs

OLEDs according to the invention and OLEDs in accordance with the prior art are produced by a general process in accordance with WO 2004/058911, which is adapted to the circumstances described here (layer-thickness variation, materials).

The data of various OLEDs are presented in Examples V1, E1-E12 below (see Tables 1 and 2). Glass plates coated with structured ITO (indium tin oxide) in a thickness of 50 nm are coated with 20 nm of PEDOT:PSS (poly(3,4-ethylenedioxythiophene)poly(styrenesulfonate), purchased as CLEVIOS™ P VP AI 4083 from Heraeus Precious Metals GmbH, Germany, applied by spin coating from aqueous solution) for improved processing. These coated glass plates form the substrates to which the OLEDs are applied. The OLEDs have in principle the following layer structure: substrate/hole-transport layer (HTL)/interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer having a thickness of 100 nm. The precise structure of the OLEDs is shown in Table 1. The materials required for the production of the OLEDs are shown in Table 3.

All materials are applied by thermal vapour deposition in a vacuum chamber. The emission layer here always consists of at least one matrix material (host material) and an emitting dopant (emitter), which is admixed with the matrix material or materials in a certain proportion by volume by co-evaporation. An expression such as DAB1:VCbz1:TEG1 (65%:30%:5%) here means that material DAB1 is present in the layer in a proportion by volume of 65%, VCbz1 is present in the layer in a proportion of 30% and TEG1 is present in the layer in a proportion of 5%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines), assuming Lambert emission characteristics, are determined. The electroluminescence spectra are determined at a luminous density of 1000 cd/m$^2$, and the CIE 1931 x and y colour coordinates are calculated therefrom. The expression U1000 in Table 2 denotes the voltage required for a luminous density of 1000 cd/m$^2$. CE1000 and PE1000 denote the current and power efficiencies achieved at 1000 cd/m$^2$. Finally, EQE1000 denotes the external quantum efficiency at an operating luminous density of 1000 cd/m$^2$.

The data of the various OLEDs are summarised in Table 2. Some of the examples are explained in greater detail below in order to illustrate the advantages of the compounds according to the invention. However, it should be pointed out that this only represents a selection of the data shown in Table 2.

Use of Compounds According to the Invention as Matrix Materials in Phosphorescent OLEDs If materials according to the invention are used as matrix for phosphorescent green dopants, very good efficiencies are obtained. With compound DAB1, for example, an external quantum efficiency of 18.3% and a power efficiency of 52 lm/W are achieved (Example E1). Mixed with the dimer of a bridged carbazole VCbz1, even 19.2% and 59 lm/W are achieved (Example E3). Furthermore, good lifetimes are obtained with compounds according to the invention. If, for example, the OLED from Example E1 is operated at a current density of 20 mA/cm$^2$, the luminous density drops to 70% of its initial value within 120 h.

If the diazaborole DAB7, which is not substituted by a heteroaromatic group, is used, higher operating voltages and lower efficiencies are obtained than with the comparable compounds according to the invention DAB1 and DAB2 (Example V1).

TABLE 1

Structure of the OLEDs

| Ex. | HTL Thickness | IL Thickness | EBL Thickness | EML Thickness | HBL Thickness | ETL Thickness | EIL Thickness |
|---|---|---|---|---|---|---|---|
| V1 | SpA1 70 nm | HATCN 5 nm | SpMA1 90 nm | DAB7:TEG1 (90%:10%) 30 nm | IC1 10 nm | ST1:LiQ (50%:50%) 30 nm | — |
| E1 | SpA1 70 nm | HATCN 5 nm | SpMA1 90 nm | DAB1:TEG1 (90%:10%) 30 nm | IC1 10 nm | ST1:LiQ (50%:50%) 30 nm | — |
| E2 | SpA1 70 nm | HATCN 5 nm | SpMA1 90 nm | DAB1:TEG1 (90%:10%) 30 nm | — | ST1:LiQ (50%:50%) 40 nm | — |
| E3 | SpA1 70 nm | HATCN 5 nm | SpMA1 90 nm | DAB1:VCbz1:TEG1 (65%:30%:5%) 30 nm | IC1 10 nm | ST1:LiQ (50%:50%) 30 nm | — |
| E4 | SpA1 70 nm | HATCN 5 nm | SpMA1 90 nm | DAB2:TEG1 (90%:10%) 30 nm | IC1 10 nm | ST1:LiQ (50%:50%) 30 nm | — |
| E5 | SpA1 70 nm | HATCN 5 nm | SpMA1 90 nm | DAB2:TEG1 (90%:10%) 30 nm | — | ST1:LiQ (50%:50%) 40 nm | — |
| E6 | SpA1 70 nm | HATCN 5 nm | SpMA1 90 nm | DAB2:VCbz1:TEG1 (65%:30%:5%) 30 nm | IC1 10 nm | ST1:LiQ (50%:50%) 30 nm | — |
| E7 | SpA1 70 nm | HATCN 5 nm | SpMA1 90 nm | DAB3:TEG1 (90%:10%) 30 nm | IC1 10 nm | ST1:LiQ (50%:50%) 30 nm | — |
| E8 | SpA1 70 nm | HATCN 5 nm | SpMA1 90 nm | DAB4:TEG1 (90%:10%) 30 nm | IC1 10 nm | ST1:LiQ (50%:50%) 30 nm | — |
| E9 | SpA1 70 nm | HATCN 5 nm | SpMA1 90 nm | DAB5:TEG1 (90%:10%) 30 nm | IC1 10 nm | ST1:LiQ (50%:50%) 30 nm | — |
| E10 | SpA1 70 nm | HATCN 5 nm | SpMA1 90 nm | DAB6:TEG1 (90%:10%) 30 nm | IC1 10 nm | ST1:LiQ (50%:50%) 30 nm | — |

TABLE 1-continued

Structure of the OLEDs

| Ex. | HTL Thickness | IL Thickness | EBL Thickness | EML Thickness | HBL Thickness | ETL Thickness | EIL Thickness |
|---|---|---|---|---|---|---|---|
| E11 | SpA1 70 nm | HATCN 5 nm | SpMA1 90 nm | DAB6:VCbz1:TEG1 (65%:30%:5%) 30 nm | IC1 10 nm | ST1:LiQ (50%:50%) 30 nm | — |
| E12 | SpA1 70 nm | HATCN 5 nm | SpMA1 90 nm | IC1:TEG1 (90%:10%) 30 nm | — | DAB1 40 nm | LiQ 3 nm |

TABLE 2

Data of the OLEDs

| Ex. | U1000 (V) | CE1000 (cd/A) | PE1000 (lm/W) | EQE 1000 | CIE x/y at 1000 cd/m$^2$ |
|---|---|---|---|---|---|
| V1  | 4.9 | 37 | 24 | 9.8%  | 0.34/0.64 |
| E1  | 3.9 | 66 | 52 | 18.3% | 0.33/0.63 |
| E2  | 3.6 | 58 | 51 | 16.5% | 0.33/0.63 |
| E3  | 3.7 | 70 | 59 | 19.2% | 0.32/0.63 |
| E4  | 4.3 | 62 | 45 | 17.1% | 0.33/0.63 |
| E5  | 4.1 | 59 | 45 | 16.4% | 0.33/0.63 |
| E6  | 3.8 | 64 | 52 | 17.6% | 0.32/0.63 |
| E7  | 3.5 | 61 | 55 | 17.0% | 0.33/0.63 |
| E8  | 4.2 | 60 | 44 | 16.6% | 0.33/0.63 |
| E9  | 3.8 | 63 | 52 | 17.4% | 0.33/0.63 |
| E10 | 4.1 | 60 | 46 | 16.8% | 0.33/0.63 |
| E11 | 3.9 | 64 | 52 | 17.9% | 0.32/0.63 |
| E12 | 4.0 | 59 | 46 | 16.3% | 0.33/0.63 |

TABLE 3

Structural formulae of the materials for the OLEDs

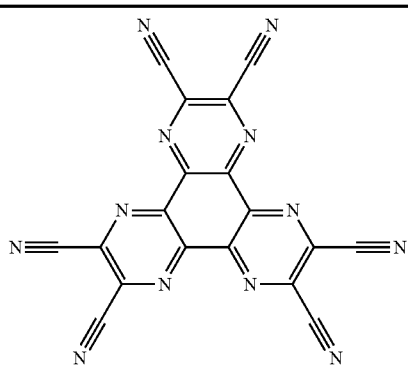

HATCN

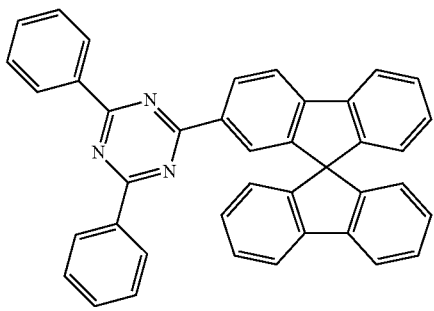 [SMILES: c1ccc(-c2nc(-c3ccccc3)nc(-c3ccc4c(c3)C3(c5ccccc5-c5ccccc53)c3ccccc3-4)n2)cc1]

ST1

TABLE 3-continued

Structural formulae of the materials for the OLEDs

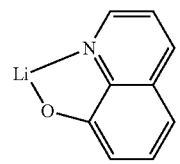

LiQ

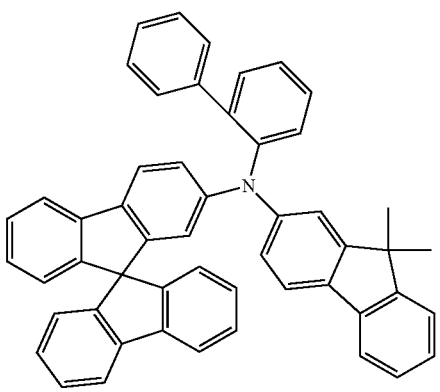 [SMILES: CC1(C)c2ccccc2-c2ccc(N(c3ccc4c(c3)C3(c5ccccc5-c5ccccc53)c3ccccc3-4)c3ccccc3-c3ccccc3)cc21]

SpMA1

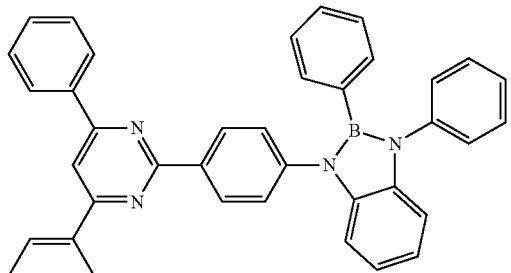

DAB1

TABLE 3-continued
Structural formulae of the materials for the OLEDs
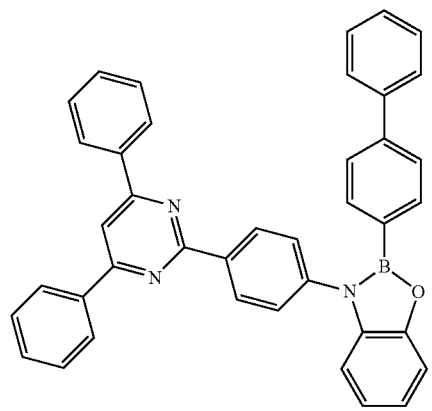 [SMILES: c1ccc(-c2ccc(B3Oc4ccccc4N3c3ccc(-c4nc(-c5ccccc5)cc(-c5ccccc5)n4)cc3)cc2)cc1]
DAB3
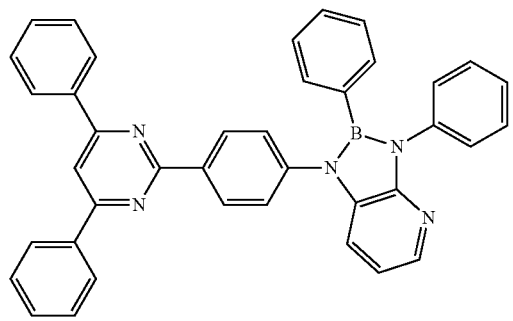 [SMILES: c1ccc(B2N(c3ccc(-c4nc(-c5ccccc5)cc(-c5ccccc5)n4)cc3)c3cccnc3N2c2ccccc2)cc1]
DAB5
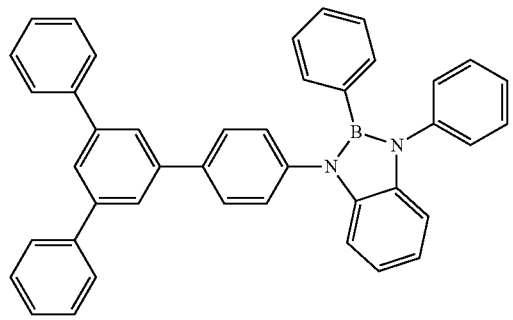 [SMILES: c1ccc(B2N(c3ccccc3)c3ccccc3N2c2ccc(-c3cc(-c4ccccc4)cc(-c4ccccc4)c3)cc2)cc1]
DAB7 (prior art)
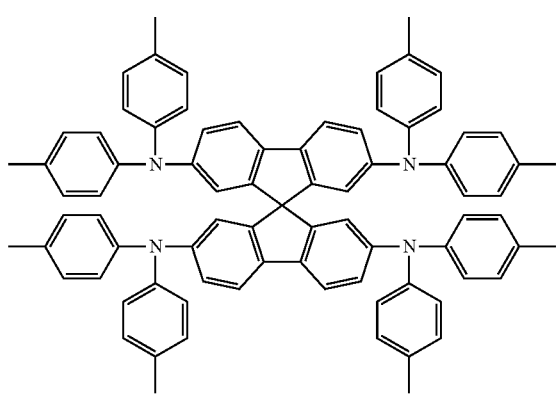
SpA1
TABLE 3-continued
Structural formulae of the materials for the OLEDs
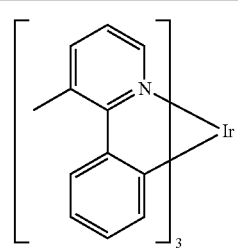
TEG1
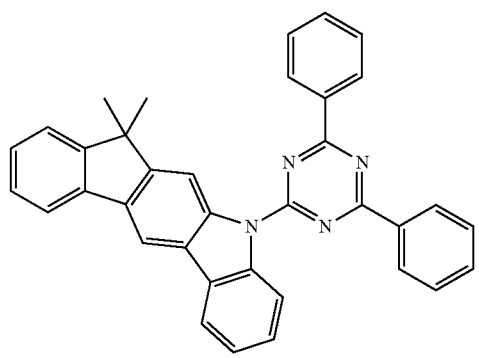 [SMILES: CC1(C)c2ccccc2-c2cc3c4ccccc4n(-c4nc(-c5ccccc5)nc(-c5ccccc5)n4)c3cc21]
IC1
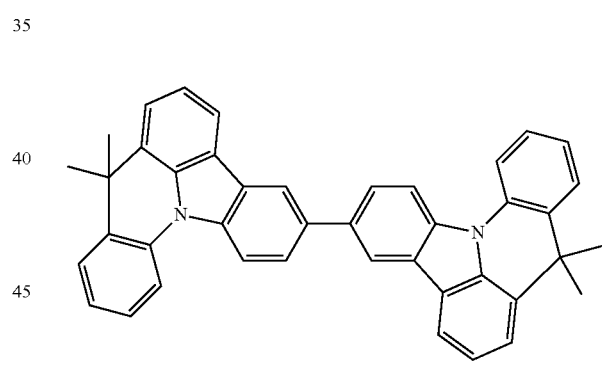
VCbz1
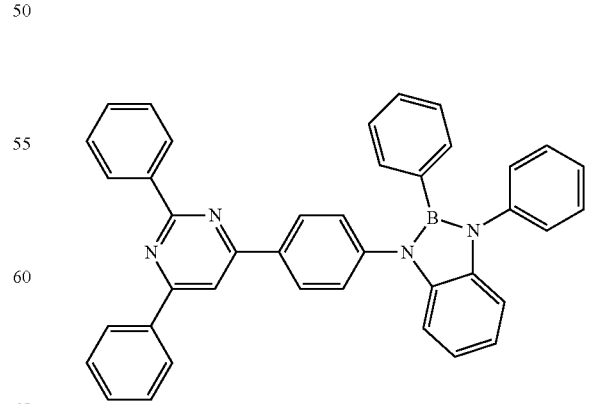
DAB2

TABLE 3-continued

Structural formulae of the materials for the OLEDs

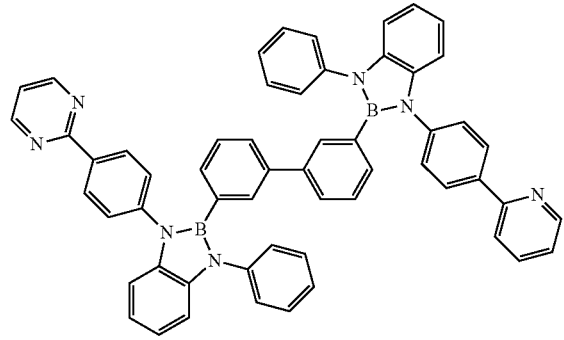 [SMILES: c1ccc(N2B(c3cccc(-c4cccc(B5N(c6ccccc6)c6ccccc6N5c5ccc(-c6ncccn6)cc5)c4)c3)N(c3ccc(-c4ccccn4)cc3)c3ccccc32)cc1]

DAB4

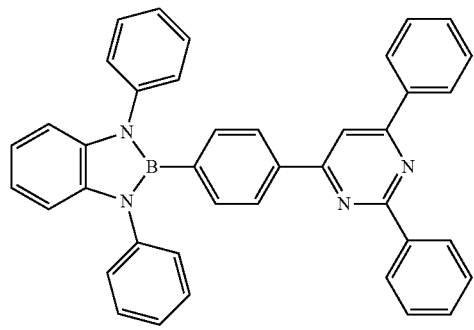 [SMILES: c1ccc(-c2cc(-c3ccc(B4N(c5ccccc5)c5ccccc5N4c4ccccc4)cc3)nc(-c3ccccc3)n2)cc1]

DAB6

The invention claimed is:

1. A compound of the formula (1),

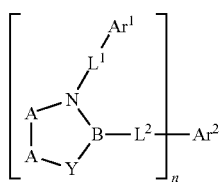

formula (1)

where the following applies to the symbols and indices used:

A-A is, identically or differently on each occurrence, a unit of the formula (2), (3), (4), (5), (6), (7) or (8),

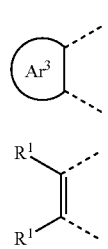

formula (2)

formula (3)

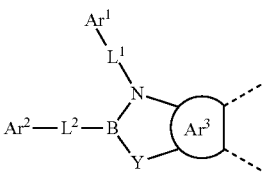

formula (4)

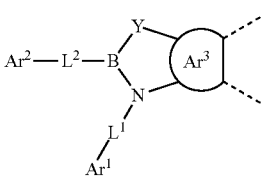

formula (5)

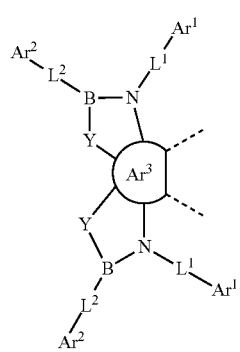

formula (6)

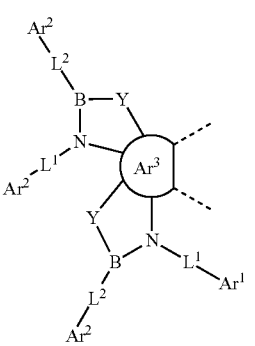

formula (7)

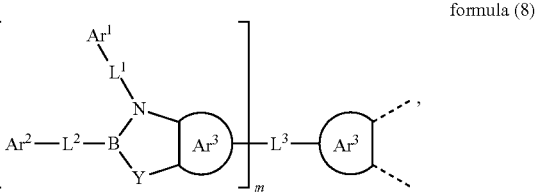

formula (8)

where the dashed bond in each case represents the link to N or Y;

Y is, identically or differently on each occurrence, N—R$^2$, O or S;

Ar$^1$, Ar$^2$ is on each occurrence, identically or differently, an aryl or heteroaryl group having 5 to 18 aromatic ring atoms, which is optionally substituted by one or more radicals R$^1$;

Ar$^3$ is on each occurrence, identically or differently, an aryl or heteroaryl group having 5 to 14 aromatic ring atoms, which is optionally substituted by one or more radicals R$^1$;

L$^1$, L$^2$ is on each occurrence, identically or differently, a single bond or a divalent aromatic or heteroaromatic ring system having 5 to 24 aromatic ring atoms, which is optionally substituted by one or more radicals R$^1$;

L³ is a single bond or a divalent, trivalent or tetravalent group;

R¹ is selected on each occurrence, identically or differently, from the group consisting of H, D, F, Cl, Br, I, CN, NO₂, N(R³)₂, C(=O)R³, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals R³, where one or more non-adjacent CH₂ groups is optionally replaced by R³C=CR³, C≡C, Si(R³)₂, Ge(R³)₂, Sn(R³)₂, C=O, C=S, C=Se, C=NR³, P(=O)(R³), SO, SO₂, NR³, O, S or CONR³ and where one or more H atoms is optionally replaced by D, F, Cl, Br, I, CN or NO₂, an aromatic or heteroaromatic ring system having 5 to 60 aromatic ring atoms, which may in each case be substituted by one or more radicals R³, an aryloxy or heteroaryloxy group having 5 to 60 aromatic ring atoms, which is optionally substituted by one or more radicals R³, or a combination of these systems, where two or more adjacent substituents R¹ may optionally form a monocyclic or polycyclic, aliphatic, aromatic or heteroaromatic ring system, which is optionally substituted by one or more radicals R³;

R² is selected on each occurrence, identically or differently, from the group consisting of a straight-chain alkyl group having 1 to 40 C atoms or a branched or cyclic alkyl group having 3 to 40 C atoms, each of which is optionally substituted by one or more radicals R³, where one or more non-adjacent CH₂ groups is optionally replaced by R³C=CR³, C≡C or C=O and where one or more H atoms is optionally replaced by D, F, Cl, Br, I, CN or NO₂, an aromatic or heteroaromatic ring system having 5 to 60 aromatic ring atoms, which may in each case be substituted by one or more radicals R³, or a combination of these systems; the R¹ and R² that are adjacent to one another in the 1,2-position may optionally form a monocyclic or polycyclic, aliphatic, aromatic or heteroaromatic ring system here, which be substituted by one or more radicals R³;

R³ is selected from the group consisting of H, D, F, CN, aliphatic hydrocarbon radical having 1 to 20 C atoms, aromatic or heteroaromatic ring system having 5 to 30 aromatic ring atoms, in which one or more H atoms is optionally replaced by D, F, Cl, Br, I or CN, where two or more adjacent substituents R³ may form a mono- or polycyclic, aliphatic, aromatic or heteroaromatic ring system with one another;

n is 1, 2, 3, 4, 5 or 6;

m is 1 if L³ is a single bond or a divalent group, or is 2 if L³ is a trivalent group, or is 3 if L³ is a tetravalent group;

wherein at least one group Ar¹ or Ar² is present which stands for an electron-deficient heteroaryl group selected from triazine, pyridine, pyrimidine, pyrazine, pyridazine, imidazole, triazole, oxadiazole or benzimidazole, each of which is bonded to L¹ and L² respectively via any desired position and which may be substituted by one or more radicals R¹.

2. The compound according to claim 1, wherein Ar³ stands, identically or differently on each occurrence, for an aryl or heteroaryl group having 5 to 10 aromatic ring atoms, which may in each case be substituted by one or more radicals R¹.

3. The compound according to claim 1, wherein Ar³ stands, identically or differently on each occurrence, for benzene, pyridine, pyrimidine, pyridazine, pyrazine, furan, thiophene, pyrrole, naphthalene, phenanthrene, quinoline, isoquinoline, quinoxaline, indole, benzofuran or benzothiophene, each of which is optionally substituted by one or more radicals R¹.

4. The compound according to claim 1, wherein the compound is selected from the compounds of the formulae (9) to (18)

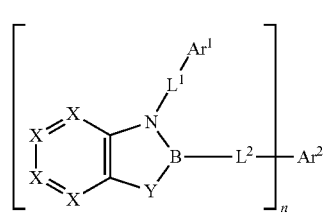

Formula (9)

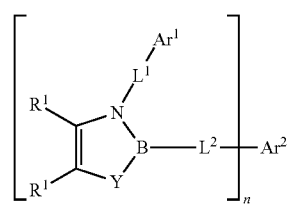

Formula (10)

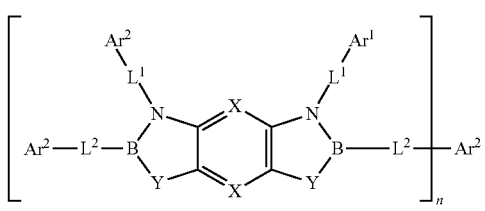

Formula (11)

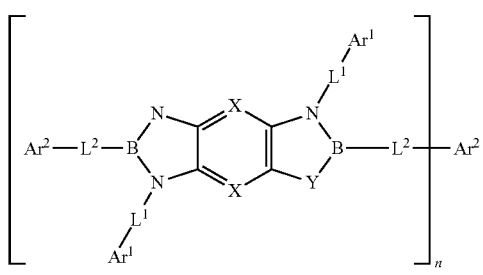

Formula (12)

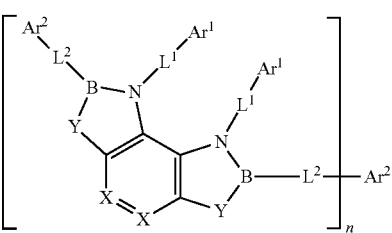

Formula (13)

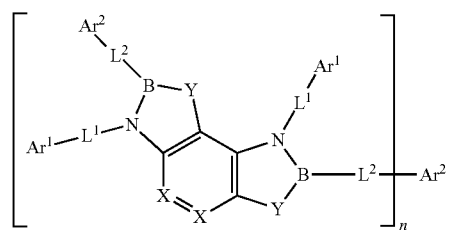

Formula (14)

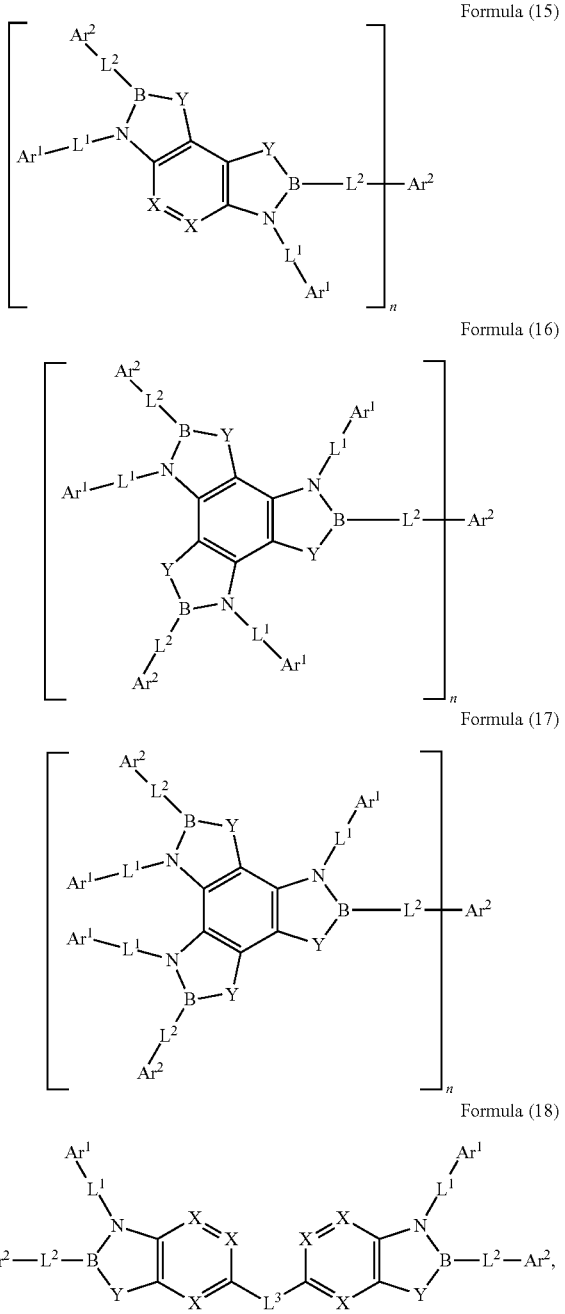

Formula (15)

Formula (16)

Formula (17)

Formula (18)

where X is on each occurrence, identically or differently, CR$^1$ or N and the other the symbols and indices used have the meanings given in claim 1.

5. The compound according to claim 4, wherein R$^2$ is selected on each occurrence, identically or differently, from the group consisting of an aromatic or heteroaromatic ring system having 5 to 30 aromatic ring atoms, which may in each case be substituted by one or more radicals R$^3$; the R$^1$ and R$^2$ that are adjacent to one another in the 1,2-position may optionally form phenyl, naphthyl, biphenyl, terphenyl or quaterphenyl, each of which is optionally substituted by one or more radicals R$^3$.

6. The compound according to claim 4, wherein
Y is, identically or differently on each occurrence, for N—R$^2$;
L$^1$, L$^2$ is, identically or differently on each occurrence, a single bond or a divalent arylene or heteroarylene group having 5 to 10 aromatic ring atoms, which may in each case be substituted by one or more radicals R$^1$;
L$^3$ is a single bond, O, S, NR$^2$, an alkylene group having 1 to 10 C atoms, which is optionally substituted by one or more radicals R$^3$, or an aromatic or heteroaromatic ring system having 5 to 30 aromatic ring atoms, which is optionally substituted by one or more radicals R$^3$;
X is on each occurrence, identically or differently, CR$^1$ or N, where a maximum of two symbols X in each ring stand for N and the other symbols X stand, identically or differently on each occurrence, for CR$^1$;
n is 1, 2, 3 or 4;
R$^1$ is selected, identically or differently on each occurrence, from the group consisting of H, D, F, CN, N(R$^3$)$_2$, a straight-chain alkyl or alkoxy group having 1 to 20 C atoms or a branched or cyclic alkyl or alkoxy group having 3 to 20 C atoms or an alkenyl group having 2 to 20 C atoms, each of which is optionally substituted by one or more radicals R$^3$, where one or more non-adjacent CH$_2$ groups is optionally replaced by R$^3$C═C R$^3$ or O and where one or more H atoms is optionally replaced by D or F, an aromatic or heteroaromatic ring system having 5 to 30 aromatic ring atoms, which may in each ease be substituted by one or more radicals R$^3$, an aryloxy or heteroaryloxy group having 5 to 30 aromatic ring atoms, which is optionally substituted by one or more radicals R$^3$, or a combination of these systems, where two or more adjacent substituents R$^1$ may optionally form a monocyclic or polycyclic, aliphatic, aromatic or heteroaromatic ring system, which is optionally substituted by one or more radicals R$^3$;
R$^2$ is selected on each occurrence, identically or differently, from the group consisting of an aromatic or heteroaromatic ring system having 5 to 30 aromatic ring atoms, which may in each case be substituted by one or more radicals R$^3$; the R$^1$ and R$^2$ that are adjacent to one another in the 1,2-position may optionally form a monocyclic or polycyclic, aliphatic, aromatic or heteroaromatic ring system here, which is optionally substituted by one or more radicals R$^3$.

7. The compound according to claim 6, wherein
n is 1, 2 or 3.

8. The compound according to claim 1, wherein Y stands, identically or differently on each occurrence, for N—R$^2$.

9. The compound according to claim 1, wherein L$^1$ or L$^2$ stands, identically or differently on each occurrence, for a single bond or a divalent arylene or heteroarylene group having 5 to 10 aromatic ring atoms, which may in each case be substituted by one or more radicals R$^1$.

10. The compound according to claim 1, wherein L$^1$ or L$^2$ stands, identically or differently on each occurrence, for a single bond or a 1,2-, 1,3- or 1,4-phenylene, pyridine, pyrimidine or triazine, each of which is optionally substituted by one or more radicals R$^1$.

11. The compound according to claim 1, wherein Ar$^1$ and Ar$^2$ are in each case one or more groups selected from benzene, pyridine, pyrimidine, pyridazine, pyrazine, triazine, pyrrole, thiophene, furan, imidazole, indole, benzothiophene, benzofuran, benzimidazole, carbazole, dibenzofuran or dibenzothiophene, each of which is optionally substituted by one or more radicals R$^1$ wherein at least one group Ar$^1$ or Ar$^2$ is present which stands for an electron-deficient heteroaryl group selected from triazine, pyridine, pyrimidine, pyrazine, pyridazine, imidazole, triazole, oxadiazole or benzimidazole, each of which is bonded to L$^1$ and L² respectively via any desired position and which may be substituted by one or more radicals R¹.

12. The compound according to claim 1, wherein $R^2$ is selected on each occurrence, identically or differently, from the group consisting of an aromatic or heteroaromatic ring system having 5 to 30 aromatic ring atoms, which may in each case be substituted by one or more radicals $R^3$; the $R^1$ and $R^2$ that are adjacent to one another in the 1,2-position may optionally form a monocyclic or polycyclic, aliphatic, aromatic or heteroaromatic ring system here, which is optionally substituted by one or more radicals $R^3$.

13. A mixture comprising at least one compound according to claim 1 and at least one further compound.

14. A formulation comprising at least one compound according to claim 1 and one or more solvents.

15. A process for the preparation of the compound according to claim 1 which comprises reacting an aromatic ortho-diamino compound with an aryl- or heteroarylboron compound in which the boron atom is substituted by two reactive leaving groups.

16. An electronic device which comprises the compound according to claim 1.

17. The electronic device as claimed in claim 16, wherein the device is selected from the group consisting of an organic electroluminescent device, an organic integrated circuit, an organic field-effect transistor, an organic thin-film transistor, an organic light-emitting transistor, an organic solar cell, an organic dye-sensitised solar cell, an organic optical detector, an organic photoreceptor, an organic field-quench device, a light-emitting electrochemical cell, an organic laser diode and an organic plasmon emitting device.

18. An organic electroluminescent device, which comprises the compound according to claim 1 is employed as matrix material for fluorescent or phosphorescent emitters and/or in an electron-transport layer and/or in a hole-blocking layer and/or in an electron-blocking or exciton-blocking layer and/or in a hole-transport layer.

* * * * *